United States Patent
Parmar (12)

(10) Patent No.: US 10,737,061 B2
(45) Date of Patent: Aug. 11, 2020

(54) ADVANCED ELECTROMAGNETIC MOTION AND TRACKING PERIPHERALLY INSERTED CENTRAL VENOUS CATHETER SYSTEM WITH EXTENDED ENDOVASCULAR APPLICATIONS

(71) Applicant: Jaywant P. Parmar, San Luis Obispo, CA (US)

(72) Inventor: Jaywant P. Parmar, San Luis Obispo, CA (US)

(73) Assignee: Jaywant P. Parmar, San Luis Obispo, CA (US)

( * ) Notice: Subject to any disclaimer, the term of this patent is extended or adjusted under 35 U.S.C. 154(b) by 978 days.

(21) Appl. No.: 14/834,342

(22) Filed: Aug. 24, 2015

(65) Prior Publication Data

US 2016/0096003 A1    Apr. 7, 2016

Related U.S. Application Data

(60) Provisional application No. 62/041,007, filed on Aug. 22, 2014.

(51) Int. Cl.
*A61M 25/01* (2006.01)
*A61M 25/09* (2006.01)
(Continued)

(52) U.S. Cl.
CPC ..... *A61M 25/0127* (2013.01); *A61M 25/0111* (2013.01); *A61M 25/09041* (2013.01);
(Continued)

(58) Field of Classification Search
CPC .............. A61B 34/30; A61B 2034/301; A61B 2034/731; A61M 2025/0681; A61M 2025/09175; A61M 25/0111; A61M 25/0127; A61M 25/09041; A61M 2025/0293; A61M 2039/087; A61M 2240/00; A61M 25/0158; A61M 25/02; A61M 25/09; A61M 29/00; A61M 39/08; A61M 39/1011; H04N 21/426;
(Continued)

(56) References Cited

U.S. PATENT DOCUMENTS 5,195,978 A     3/1993  Schiffer
5,464,023 A  *  11/1995 Viera ................ A61M 25/0127
                                                    600/434
(Continued)

FOREIGN PATENT DOCUMENTS

RU      2218191 C2    12/2003

OTHER PUBLICATIONS

Communication from the International Searching Authority including Communication relating to the results of the Partial International Search from PCT/US2015/046610.
(Continued)

*Primary Examiner* — Brandy S Lee
(74) *Attorney, Agent, or Firm* — Frank Rosenberg

(57) ABSTRACT

A method of inserting a catheter and catheter placement apparatus that were designed for improving the safety and efficiency in the placement of a PICC (Peripherally Inserted Central Catheter) implant are described. The invention enables placement of the catheter into the body while the catheter is maintained in a sterile environment.

22 Claims, 9 Drawing Sheets

(51) Int. Cl.
  *A61B 34/00* (2016.01)
  *A61M 25/06* (2006.01)
  *A61B 34/30* (2016.01)
(52) U.S. Cl.
  CPC ......... *A61B 34/30* (2016.02); *A61B 2034/301* (2016.02); *A61B 2034/731* (2016.02); *A61M 2025/0681* (2013.01); *A61M 2025/09175* (2013.01)

(58) Field of Classification Search
  CPC .. H04N 21/45; H04N 21/466; H04N 21/4722; H04N 21/482; H04N 21/4826; H04N 21/4828
  See application file for complete search history.

(56) References Cited

U.S. PATENT DOCUMENTS

| | | | | |
|---|---|---|---|---|
| 5,579,780 | A * | 12/1996 | Zadini | A61M 25/09041 600/585 |
| 6,656,199 | B1 * | 12/2003 | Lafontaine | A61M 25/0127 606/191 |
| 6,911,026 | B1 * | 6/2005 | Hall | A61B 17/22 128/899 |
| 7,901,444 | B2 | 3/2011 | Slavas | |
| 7,992,573 | B2 | 8/2011 | Wilson | |
| 8,283,155 | B2 | 10/2012 | Holmes et al. | |
| 8,882,701 | B2 | 11/2014 | Sucheki | |
| 2003/0208188 | A1 | 11/2003 | Ritter | |
| 2006/0041245 | A1 | 2/2006 | Ferry | |
| 2007/0016006 | A1 * | 1/2007 | Shachar | A61B 1/00158 600/424 |
| 2009/0076445 | A1 | 3/2009 | Furnish | |
| 2009/0131798 | A1 | 3/2009 | Minar | |
| 2011/0196397 | A1 * | 8/2011 | Frantz | A61B 17/22012 606/159 |
| 2011/0257661 | A1 | 10/2011 | Choi | |
| 2011/0313516 | A1 | 12/2011 | Dang et al. | |
| 2013/0096589 | A1 | 4/2013 | Spencer | |

OTHER PUBLICATIONS

Fernstrom A., Aerobiology and its role in the transmission of infectious diseases. J. Pathog. 2013; 2013: 493960. Doi: 10.1155/2013/493960. Epub. Jan. 13, 2013.
CDC Newroom Press Release: CDC and Partners Celebrate World Health Day 2011 to Draw Attention to the Issue. Apr. 7, 2011 http://www.cdc.gov/media/releases/2011/p0407_antimicrobialresistance.html.
CDC Guidelines for the Prevention of Intravascular Catheter Related Infections, 2011.
A Multifactorial Intervention for Reducing Catheter Related Bacteremias in Intensive Care Medicine Departments. Pilot Study Report. Madrid: Ministry of Health and Consumer Affairs, 2009.
The Joint Commission. Preventing Central Line-Associated Bloodstream Infections: A Global Challenge, a Global Perspective. Oak Brook, IL: Joint Commission Resources, May 2012. http:///PreventingCLABIs.pdf.
Seldinger, Sven Ivar (1953) Catheter Replacement of the Needle in Percutaneous Arteriography: A new technique, Acta Radiologica [Old Series], 39:5, 368-376.
International Preliminary Report on Patentability from PCT/US2012/052175, dated Feb. 25, 2014.
English translation of Russian Patent No. 2218191 issued Dec. 10, 2003.
Official Action from U.S. Appl. No. 13/593,502 dated Jun. 30, 2015.
Official Action from U.S. Appl. No. 13/593,502 dated Apr. 21, 2016.
Official Action from U.S. Appl. No. 13/593,502 dated Dec. 2, 2016.
Official Action from U.S. Appl. No. 13/593,502 dated Nov. 17, 2017.
Moran J, Screening for novel risk factors related to peripherally inserted central catheter associated complications. J Hosp Med. Aug. 2014;9(8):4819. doi: 10.1002/jhm.2207. Epub Jun. 9, 2014.
Rivera AM, The history of peripheral intravenous catheters: how little plastic tubes revolutionized medicine. Acta Anaesthesiol Belg. 2005;56(3):27182.
Stuart, R.L., Peripheral intravenous catheter associated *Staphylococcus aureus* bacteraemia: more than 5 years of prospective data from two tertiary health services. Med J Aust. Jun. 3, 2013;198(10):5513.
Communication pursuant to Article 94(3) from EP application No. 15 7669 55.7 dated Nov. 14, 2018.
Second Office Action from Chinese Application No. 201580055989.9, dated Mar. 18, 2020.
Translation, Second Office Action from Chinese Application No. 201580055989.9, dated Mar. 18, 2020.

* cited by examiner

ADVANCED ELECTROMAGNETIC MOTION AND TRACKING PERIPHERALLY INSERTED CENTRAL VENOUS CATHETER SYSTEM WITH EXTENDED ENDOVASCULAR APPLICATIONS

RELATED APPLICATIONS

This application claims the benefit of priority U.S. Provisional Patent Application Ser. No. 62/041,077, filed 22 Aug. 2014.

BACKGROUND

The Changing Modern Medical Landscape

There has been an ongoing significant increase in costs of healthcare services in the modern era and globally. For example, in the United States, this is generally the net result of (1) increased supply through advances in modern medical care which have extended the capabilities of medicine, and, (2) increased demand through population base increases resulting from the synergistic effects of (a) increasing birth rates and (b) increasing life expectancy. The effects have led to exponential increases in US expenditures toward healthcare per capita and in net total. The trend is global. Thus, in modern medical practice situations, there is an urgent need to use technology toward a more efficient delivery of care in order to keep the costs of healthcare from ballooning. So-called "POC" (Point of Care) medical delivery technologies seek to advance the independence of individual practitioners and practitioner systems in delivering state of the art healthcare with maximum efficiency.

As an example of POC technologies, there are devices currently in use that utilize state-of-the-art microsensor, microcomputer and microfluidic technology to automate entire laboratory chemical testing processes that are routinely performed of the blood, urine and serum in clinical medical practice within very portable and sometimes handheld systems. These sorts of systems greatly improve healthcare efficiencies as many extra steps, which may include additional labor, extra specially trained personnel and extra resources, are removed. A recent patent application of Holmes et al. "Point-of-care fluidic systems and uses thereof" U.S. Pat. No. 8,283,155 details such a laboratory device. This sort of device replicates the services of a "bricks and mortar" medical laboratory with a single operator using single drops of blood obtained via capillary hypodermic sampling. The net effect of this technology is much more efficient medical care via elimination of many of the costly labor steps and supplies related to the standard method of body fluid laboratory testing, which generally includes patient registration, sample collection, sample transport, storage and processing, results generation, and, results reporting. All of these processes can effectively be completed through the use of the described point of care fluidic system and by a single operator. To enable such a point of care engineered system for placement of a PICC (Peripherally Inserted Central Catheter) implant, is the immediate goal of the current invention. The invention calls upon and applies a modern motion control system of novel design which allows for telecommunication integration with medical data networks. The device would enable significant increases in efficiency of PICC delivery, and, importantly, the overall safety of the procedure would be improved.

INTRODUCTION

Central venous access fluid access tubes, including central venous lines (CVL) and peripherally inserted central venous lines (PICC lines), are a fundamental element of many acute and nonacute medical scenarios [1]. Although methods to achieve durable and safe central venous access have reached a significant level of sophistication, the risk for implant contamination has generally increased in PICC line placement, in particular due to environmental droplet or contact contamination in the uncontrolled and often hostile bedside delivery environment [2]. With technologically driven expansion of medical services and healthcare development, placement of PICC has shifted from an operative surgical or angiographic suite procedure, to a bedside "point of care" procedure. Unfortunately, the tools for PICC placement have not changed to accommodate the point of care delivery. Currently, PICC catheters and implant procedure tools (namely a guidewire) need to be handled in the open environment at the bedside under maximum sterile barrier technique by a single operator during the point of care implant. The elongate and cumbersome catheters and guidewires are stored in and exposed to the open ambient environment of the bedside hospital ward for the time of placement by the single operator, which is generally about 45 minutes [3]. The number of central line and PICC infections is rising with increasing numbers of procedures. In one large multi hospital study, incidence has been measured at 10% of hospital acquired *Staphylococcus aureus* bacteremia cases [4], and, a specific PICC related proportion of all cause hospital acquired infection of 2% was observed in another large study [5]. Concurrently with increasing incidence of PICC related infection, resistant pathogen strains are becoming an increasing concern [6]. Therefore, there has been an ongoing focus of the World Health Initiatives to standardize approaches to aseptic techniques and maximum sterile barrier utilization [7, 8, 9] for central line placement.

This invention is directed toward the goal of fundamentally changing the point of care PICC implant procedure thereby bringing it to a new level of efficiency and maximum sterile barrier technique. The inventive system employs technology aimed specifically at eliminating environmental contamination through contact and airborne droplet spread to the implant. This invention utilizes one or more of the following concepts: (1) full linear and rotary actuation of a linear (or otherwise) constrained, sterile enclosed catheter and guidewire magnetically through the sterile enclosure, (2) customizable catheter terminal coupling creation via use of an integrated peel away sheath and its separable component of a compression ring construct that allows the catheter to be cut and fused to a hub at any length, and, (3) seamless network connectivity of the endovascular tool to the electronic medical record (EMR) via a networked microcomputer device such as a smartphone. Through the use of this invention, the catheter implant is never exposed to the open environment and is directly placed from a sterile fluid filled hydrostatic and hemostatically actuated enclosure directly into the patient's bloodstream without exposure to the ambient environment. The magnetic actuation is performed by a lightweight single operator, single hand operated robotic motion control system that brings added efficiencies of electronic medical record (EMR) integration to the operator through the networked platform. The motion control actuator mounts to the sterile enclosure (containing the implant) which is supported by a single operator hand or can be supported by other means (gantries, supported on the patient's bed, etc.). This leaves the other operator hand to control the local insertion site or attend to other needs. The system's immediate functionality substitutes 3 "operator hands", effectively replicating the assistance of a dedicated angiography technologist assistant in catheter manipulation, and, recreating or improving upon the traditional sterile operative environment of an angiography procedure room. Seamless integration of the EMR for the operator leads to further decrease in resource requirements of PICC delivery. Furthermore, the electromagnetic motion and tracking (EMMT) PICC technology can be adapted for placement of larger bore CVC's, and, it can also be adapted to placement of nested sheath/catheter/catheter based tool systems used for more complex endovascular procedures, such as cerebrovascular clot retrieval or coronary artery angioplasty and stenting. Flexibility of the system is achieved through use of a novel method for terminal fitting creation on the catheter tube, that allows for placement of a standard luer lock fitting, or, a hemostatic endovascular tool introduction port with a possible integrated fluid delivery port. This allows a vascular introducer sheath (instead of a PICC) to be left in place with a distally located tip in a body and a proximally located hemostatic access hub. A second system in a second configuration can be employed to work through a previously placed hemostatic access port to provide further functionality, and, thereby enable a repertoire of endovascular procedures, such as cerebrovascular clot retrieval, that could be delivered by a single device (in multiple configurations) and a single user with extreme efficiency and ease.

EMR integration is also a natural EMMT PICC system advantage, thus, there are further increases in procedural efficiency that can be obtained via the system's network connectivity at the point of care. For example, documentation of the "time out" among other documentation events can be streamlined through the EMMT PICC operator interface. Additional benefits of network connectivity include more futuristic functionality such as local first operator+remote second operator system manipulation during a procedure, which may be advantageous in battlefield situations, or, during more technically challenging procedures for which the device may be modified to accommodate, such as cerebrovascular clot removal.

The asepsis level of the procedures performed without using the EMMT PICC invention are limited by the extent and ability of current "maximum sterile barrier technique" described by CMS and JACHO, among other national and international regulatory agencies. The EMMT PICC solution achieves a new level of maximum sterile barrier technique which can only be realized through use of the motion control system that is the subject of this patent application. It is the sincere hope that the solution proposed herein will eventually significantly reduce infection rates, thereby improving clinical outcomes while simultaneously significantly improving efficiency of the healthcare delivery.

The Advanced Telerobotic EMMT PICC system is designed to be a cornerstone medical technology for future routine practice. It enables a new paradigm of endovascular procedural efficiency through a synergistic application of many technologies for a seamless electro-mechanical and network augmented single operator practice. The goals include improved patient outcomes, extreme cost efficiency and complete operator satisfaction. The tool, in its most basic form, enables a method for delivering a typical peripherally inserted central venous access catheter implant that will be the obvious "best practice" alternative.

To extend point of care technologies toward a simple and ubiquitous endovascular surgical procedure is the immediate goal of this invention. To establish a basic electromechanical method for similar and more complicated procedures is an additional goal. The inventive design improves the experience of the endovascular operator in the medical system, giving him/her the equivalent of additional "hands" for manipulating lengthy catheters, catheter based tools and guidewires with extreme precision and ease, and, with a new level of maximum sterile barrier technique. The design of the system allows the operator to manipulate, typically, two (e.g., a catheter and guidewire) endovascular tools through a typical Seldinger technique [10] based vascular access port without moving positions to grasp these tools (as is the usual method), and, with a single hand. The goal is to achieve the most efficient medical resource utilization during endovascular procedures that will be required in the future medical era.

Additional significant advantages of the proposed procedural aiding system are derived from service line delivery integration into a healthcare enterprise computer database and network. For example, as disposable supplies are used by the EMMT PICC system, automated restocking orders can be placed. The tool could alert the operator of additions to the worklist or changes in patient triage at a facility. The tool could be used to document and report events surrounding the procedure such as "time out" and consent. The tool could generate and issue procedure reports. There are a number of ways the system could be used to augment "point of care" PICC delivery through computer network integration.

SUMMARY OF THE INVENTION

In a first aspect, the invention provides a method of placing a catheter inside a body (preferably a living human body), comprising: providing an enclosed tube comprising a guidewire and one or more external magnets that are external to the enclosed tube and coupled to one or more ferromagnetic components within the enclosed tube; the enclosed tube open at one end to provide an entry to the body; moving at least one of the external magnets to provide a motive force to move at least a portion of the guidewire from inside the tube to inside the body; and moving a catheter over the guidewire into place within the body. The interior of the enclosed tube should be sterile.

In this method, preferably at least one other external magnet is coupled to one or more ferromagnetic component within the tube that is, in turn, coupled to the catheter that is also within the tube; and the at least one other external magnet is moved to provide a motive force to move at least a portion of the catheter from inside the tube to inside the body. Preferably, the one or more external magnets comprise a first external magnet that is coupled to a first ferromagnetic actuator that moves the guidewire and a second external magnet that is coupled to a second ferromagnetic actuator that moves the catheter. Preferably, the one or more external magnets provide a magnetic field that translates down the length of the sterile tube in the proximal direction toward the body, and is are rotatable around the circumference of the tube to provide rotation about the central axis of the guidewire and/or catheter within the tube. It is desirable for the catheter to be closely fitted within the enclosed tube to provide radial constraint (this improves mechanical deliverability of the device). Preferably, the enclosed tube has an inner diameter that is 50% or less, preferably 30% or less, more preferably 10% or less than the outside diameter of the catheter. Preferably, a sterile saline solution is added through the distal end of the tube.

Typically, at the end of the procedure, a portion of the catheter is (optionally) cut and a hub is attached to the distal end of the catheter; wherein the hub has a larger diameter than the catheter. Desirably the hub provides for infusion and withdrawal by standard medical fittings. The hub is typically a bulky apparatus that will be fitted to the catheter after insertion. In some preferred embodiments, the exposed end of the catheter has a fitting (for example threads or an external or internal fitting for a snap-on or snap-in) for attachment to an injection port. An externally applied adhesive tape (with or without additional heating) may optionally be used to further strengthen the seal. The catheter may have several fittings along its length so that, after placement, the catheter can be cut to a desired length and still easily be attached to an injection port.

Although the inventive methods are primarily concerned with care for humans, the invention can also be applied to non-human animals, as well as cadavers for medical research and training.

In a second aspect, the invention provides catheter placement apparatus, comprising: a sterile enclosed tube comprising: a guidewire, a first ferromagnetic component coupled to the guidewire, and a catheter; one or more external magnets that are external to the enclosed tube and coupled to one or more ferromagnetic components within the sterile tube; and wherein the largest dimension of the enclosed tube is the length direction and wherein the one or more external magnets comprises: a first external magnet that is coupled to the first ferromagnetic component that is coupled to the guidewire and wherein the first external magnet is translatable in the direction of the length of the enclosed tube. Preferably, the enclosed tube is open or openable at at least one end to provide access to a body. Preferably, the catheter placement apparatus comprises at least two external magnets, a first external magnet and a second external magnet; wherein the first external magnet is coupled to a first ferromagnetic actuator that is coupled to the guidewire and wherein the second external magnet is coupled to a second ferromagnetic actuator that is coupled to the catheter. The ferromagnetic components can be integral with the guidewire and/or catheter, or can be separate components that are joined with or in proximity to the guidewire and/or catheter such that movement of each component will move the guidewire and/or catheter with which it is coupled. In some preferred embodiments, one or more of the external magnets comprise a Halbach array of magnets. Preferably, the first external magnet and the second external magnet are translatable in the direction of the length of the enclosed tube. Also, preferably, the first external magnet or the second external magnet has a magnetic field that is rotatable in the direction around the circumference of the enclosed tube (that is, rotates in the direction that is perpendicular to tube length.

The enclosed tube need not be entirely enclosed and should be open or openable at at least one end to provide access to a body. Preferably, the mounting is designed to limit hydrostatic pressure as the tube may be filled with sterile saline that is placed in direct contiguity with the blood pool. The ferromagnetic components can be integral with the guidewire and/or catheter, or can be separate components that are joined with or in proximity to the guidewire and/or catheter such that movement of each component will move the guidewire and/or catheter with which it is coupled.

The catheter can be single or multilumen. Typical lengths for the catheter are between 10 and 150 cm; more typically between 50 and 100 cm. Typical lengths for the guidewire are between 10 and 300 cm; more typically 50 and 200 cm.

In a related aspect, the invention provides a sheath for vascular introduction having a proximal separable portion which serves as an annular constrainment ring to allow for hub fusion to an encircled catheter that is introduced through the vascular introduction sheath. An embodiment of this sheath is illustrated in FIG. 9.

In another aspect, the invention provides a method for mounting a plastic or metal hub to a bare tubular conduit to a flexible catheter using a constrainment ring incorporated into a vascular introduction sheath or to a rigid tubular catheter using an internally passing obturator, a proximal sleeve and an adhesive bonding agent. An embodiment, this method is illustrated in FIG. 8.

The invention includes each of the concepts described here and also includes any combination of the concepts described herein. Exemplary (but non-limiting) structures for accomplishing the goals of the invention are shown in the drawings. The descriptions are not to be understood as limited only to the specifically described embodiments, but are to be understood as describing features that may be part of the invention as separate features or in combination with other features of the invention.

System Advantages

Working with cumbersome catheters and guidewires in bedside procedures is difficult, especially in busy hospital environments. Sterility is a basic challenge when working with lengthy catheters and guidewires in any situation, but, keeping sterility of tools in bedside procedures is often particularly challenging mainly due to physical space limitations. The supply for PICC and other central venous catheters is often bottlenecked by basic space and time required for sterile delivery procedure technique. Additional systems based impediments compound the effect in bedside procedures (checking medicines, labs and indications, having witnessed documentation of "timeout", certification and time stamp of the procedure, documentation of post procedure proper or improper function, ordering chest x ray, notification of certified placement or need for further manipulations/reattempt, reordering supplies).

The advantages of the invention in various embodiments include one or (typically) more of the following:

Minimization of sterile prep area and prep and drape supplies;
Optimization of sterility and maneuverability even in close quarters;
Minimization of bedside environmental exposure to body fluids and blood versus unconstrained used catheters and guidewires;
Compactness and space requirements for operation of catheter and guidewire;
Lack of exposure of the catheter and guidewire to the ambient infectious environment;
Optimization of operator comfort and workflow even in close quarters;
Enablement of very controlled, tactile responsive and intuitive portable bedside procedures with one handed catheter+guidewire operation;
Maximization of connectivity to the EMR through the entire procedure process;
Maximization of efficient ordering cueing and reporting through EMR;
Minimization per patient cost;
Minimization of staffing requirements for healthcare provider systems;
Minimization of shipping and handling costs of single use expendable units;
Minimization of the carbon footprint of the medical service line through cradle to grave engineering and design of the whole product;
Improvement in patient experience of care;
Improvement in physician satisfaction and outcomes, and;

Improvement in effectiveness of IR/PICC lab utilization for PICC delivery through a very high level of EMR and health system IT network communication integration of very specific procedural level data (eg, how far did the guidewire enter the basilic vein before encountering obstruction).

Through the implementation of this advanced telerobotics EMMT PICC system, the most cost effective manner to place a PICC. It will be achieved through integration of many small and large multi system advantages that all combine to achieve a breakthrough gain in effectiveness. As a result, the per unit cost for catheter delivery will drop significantly in this important medical service line through use of the technology.

DETAILED DESCRIPTION OF AN EMMT PICC SYSTEM EMBODIMENT

Figure 1:
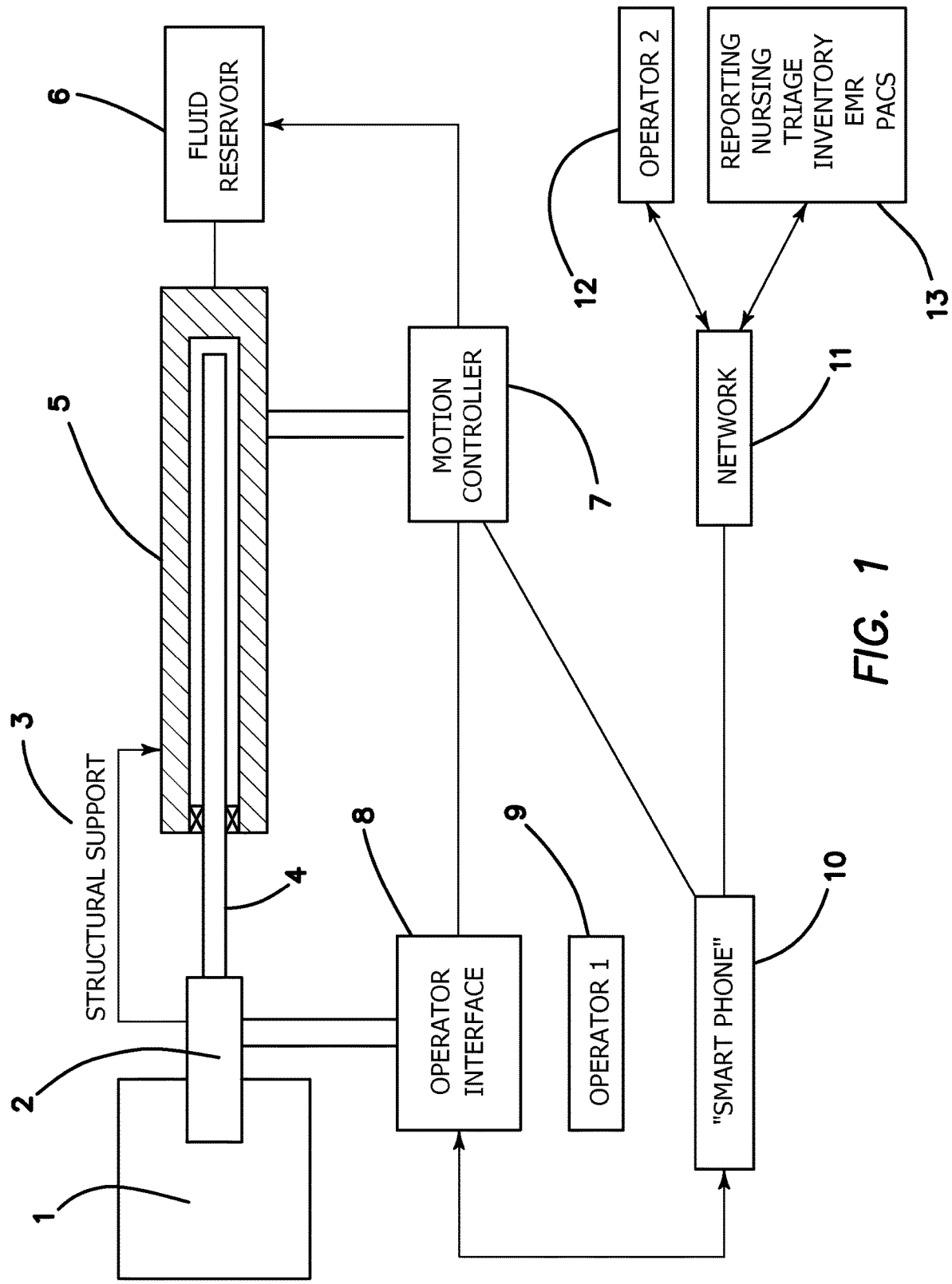
FIG. 1: Schematic view of advanced telerobotic network.

FIG. 1 represents a schematic depiction of operational features of the telerobotic platform within the medical system. The figure details the fact that the EMMT PICC device (2,3,4,5,6,7,8) is largely excluded from the sterile field (1) which includes an in place vascular introducer sheath that may or may not be of the type described in the description of the current invention. It may be entirely excluded from the sterile field beyond the hub attachment to the vascular introducer sheath in the sterile field (1). The lengthy catheter and guidewire required for the implant procedure and eventual implant are housed within a sterile enclosure (4) that can be supported by a sterile or nonsterile hand via a proximally, or otherwise, located hand grasp (2) that includes controllers for the individual catheter and guidewire motion control elements, "rotor translators" (5,7) which provide rotational and linear translational motion (relative to the hand grasp and via mechanical linkage of the hand grasp) (2) to the catheter and guidewire via magnetic coupling to these end drive elements through the sterile enclosure. The hand grasp is mechanically coupled to the motion control system through the shaft of the sterile enclosure and possibly through an additional external support that may be needed (3). Controllers for various fluid reservoirs or advanced sensors and or actuators (6) coupled via tubing or other means to the device including fluid or fluid medication administration via hydrostatic pressure infusion or suction, via electrical stimulation or detection, via optical stimulation or detection or via fluid pressure detection may also be integrated, but, these are generally not needed for PICC placement. There is a capability for a second operator (12) to assist or replace the first operator (9) through a computer network (11) to the motion control elements (7, 5) via a smartphone (10) or similar networked computer device. This is generally not needed in PICC, but, this would certainly be useful in certain endovascular workflow scenarios. In the case that the operator at the bedside (9) is completely replaced, the structural support (3) may require mounting to the patient's bed or a gantry that is linked to the patient, and, importantly, additional support at the sheath entry site at the patient's skin. However, the device (2,3,4,5,6,7,8) in its most basic form is designed to be hand supported by the bedside operator (9) who is responsible for supporting and guiding its position relative to the patient's skin and vascular introducer sheath. Additional gantry supports of the device for the single operator may be useful.

Figure 2:
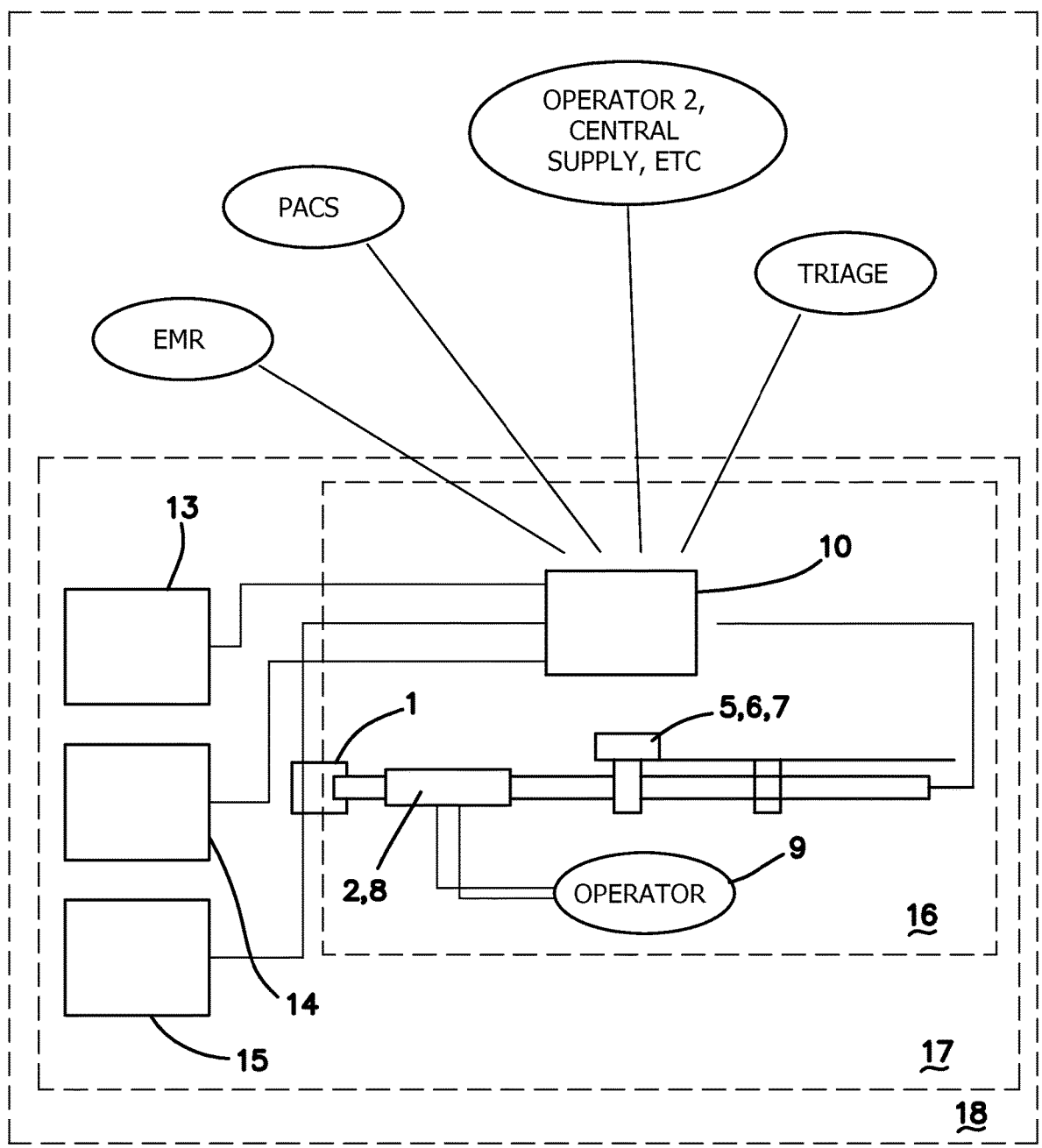
FIG. 2: Advanced telerobotic operator experience-independence, consistency and empowerment through a multi-tiered network integrated and elegantly designed mechanical "smart" instrument.
Figure 3:
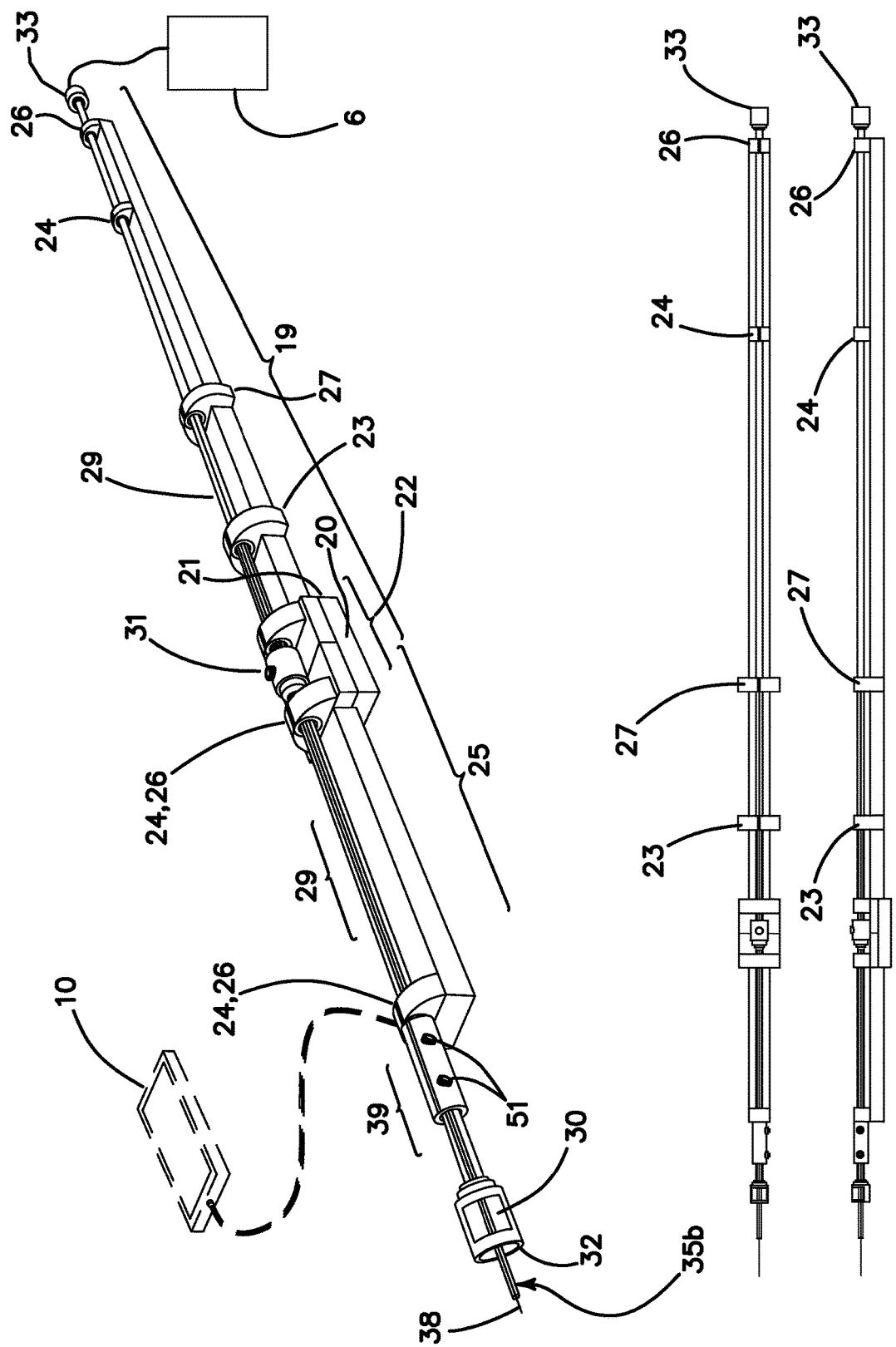
FIG. 3: Catheter placement apparatus.
Figure 4:
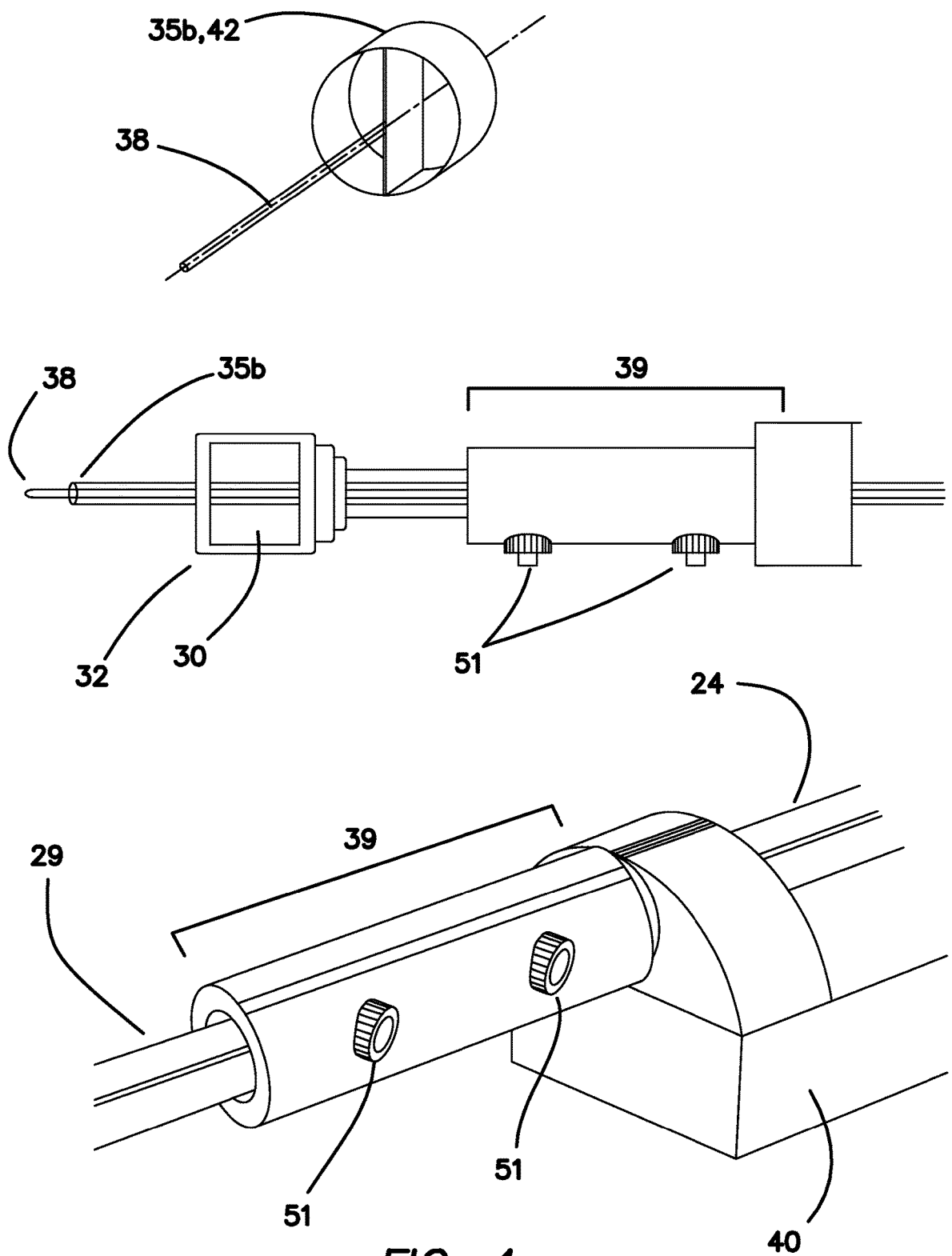
FIG. 4: Component details of apparatus.
Figure 5:
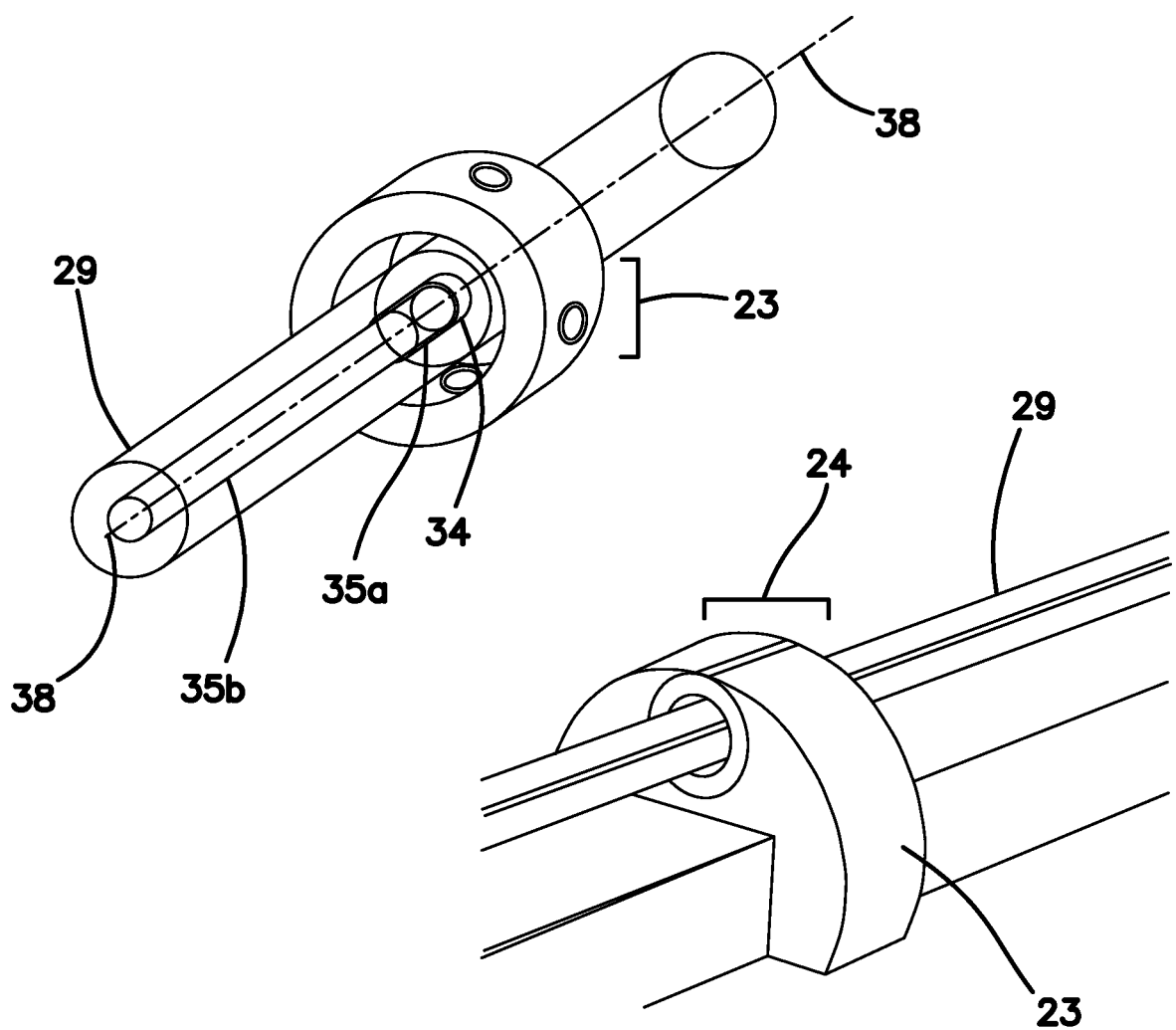
FIG. 5: Nested catheter and guidewire electromagnetic actuation sub assembly detail.
Figure 5:
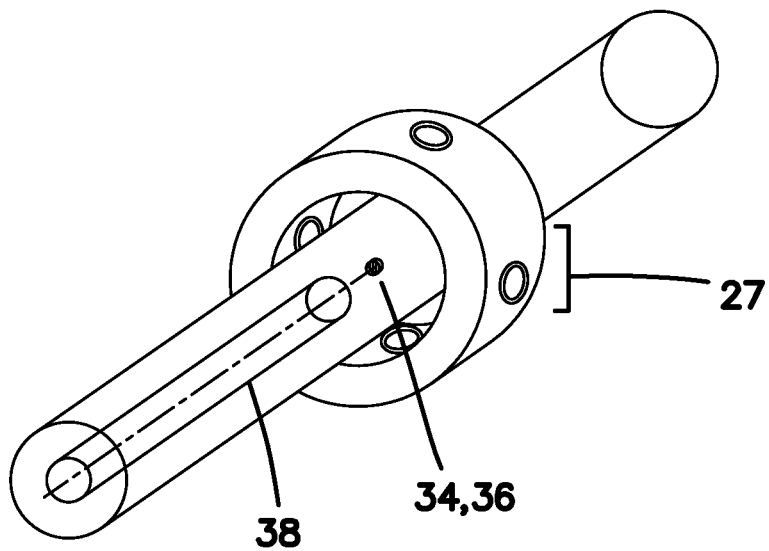
Figure 6:
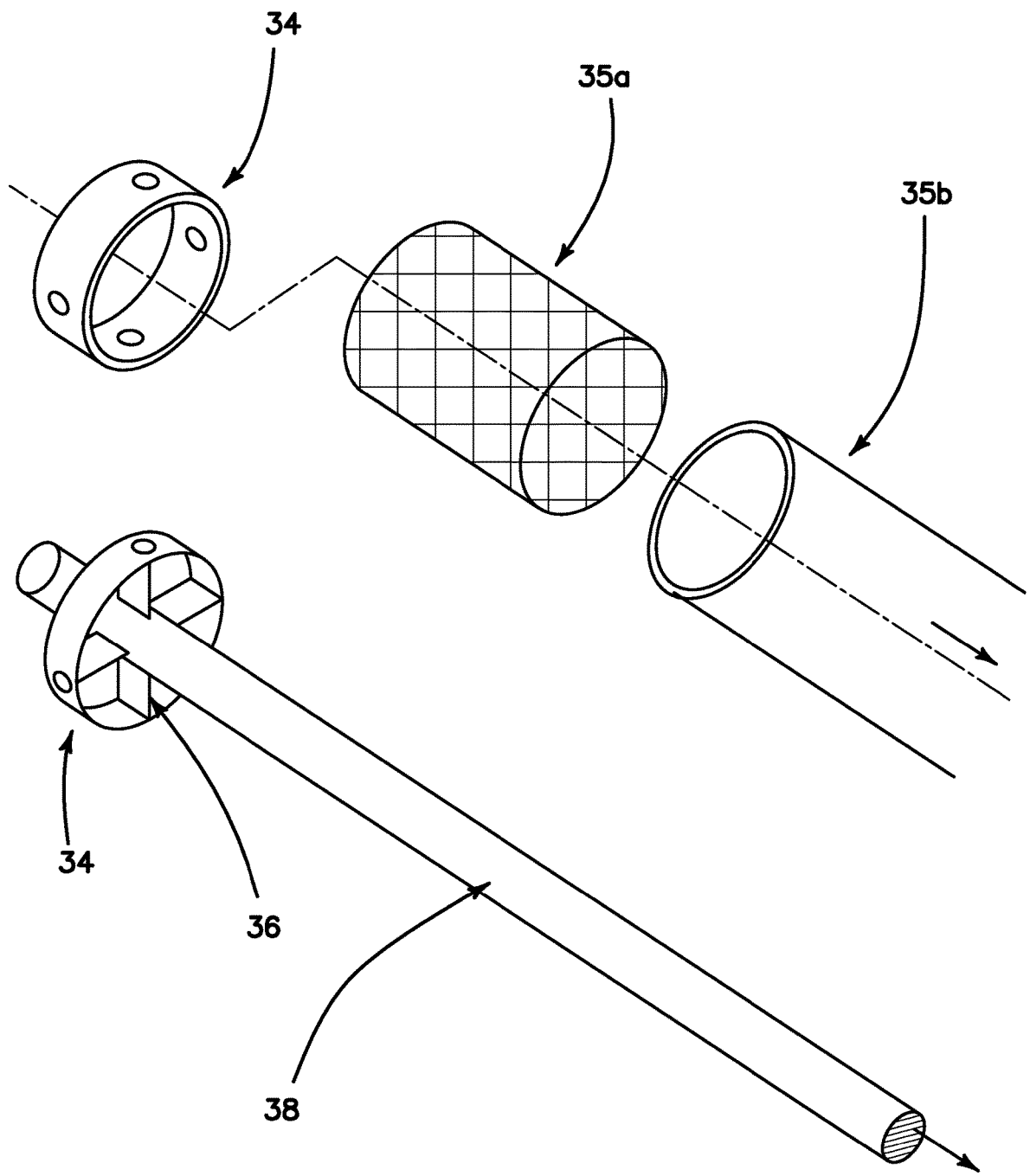
FIG. 6: View of sterile enclosed components.
Figure 7:
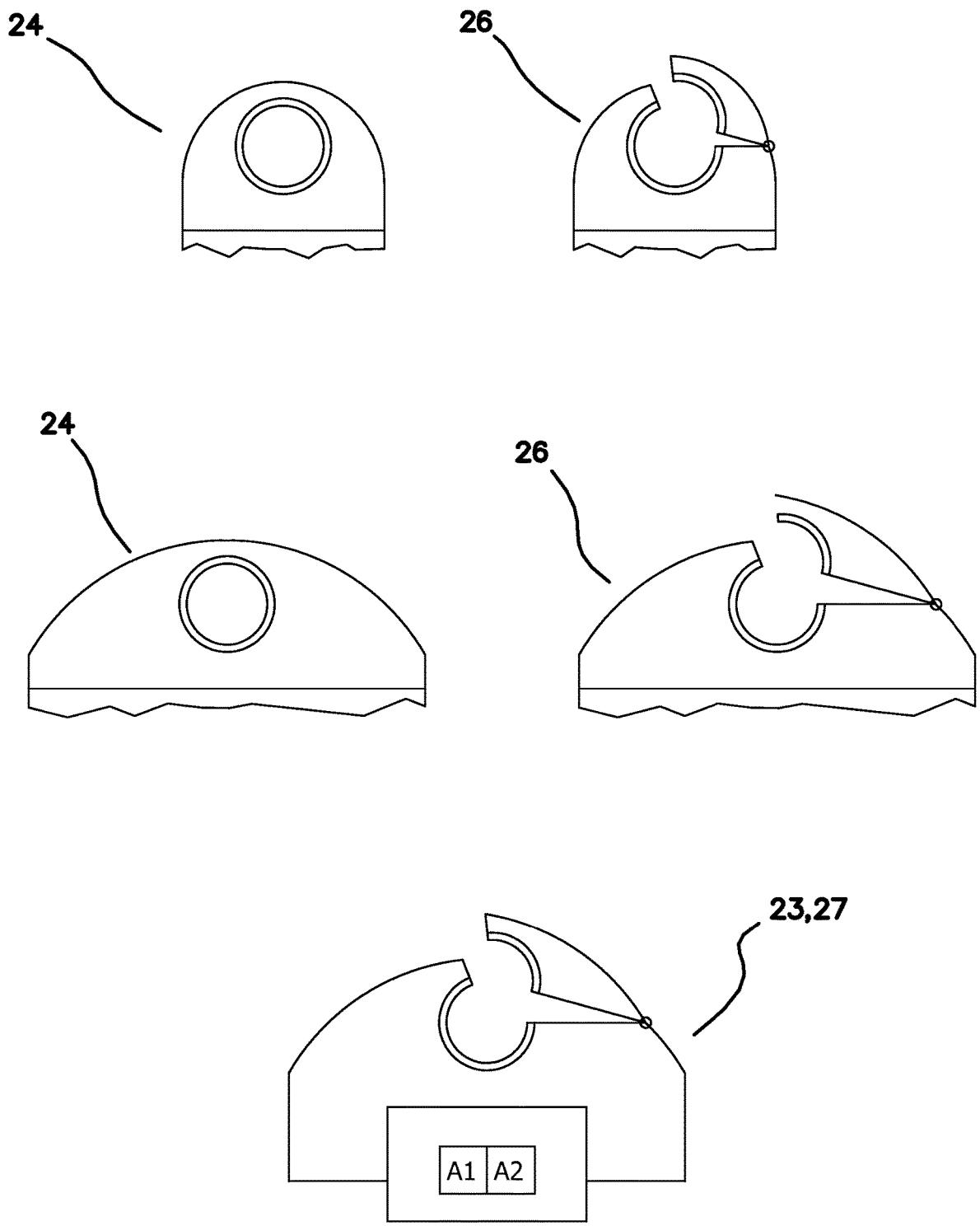
FIG. 7: Linear constrainment guides-moveable vs fixed, perforated vs through-bore.
Figure 8:
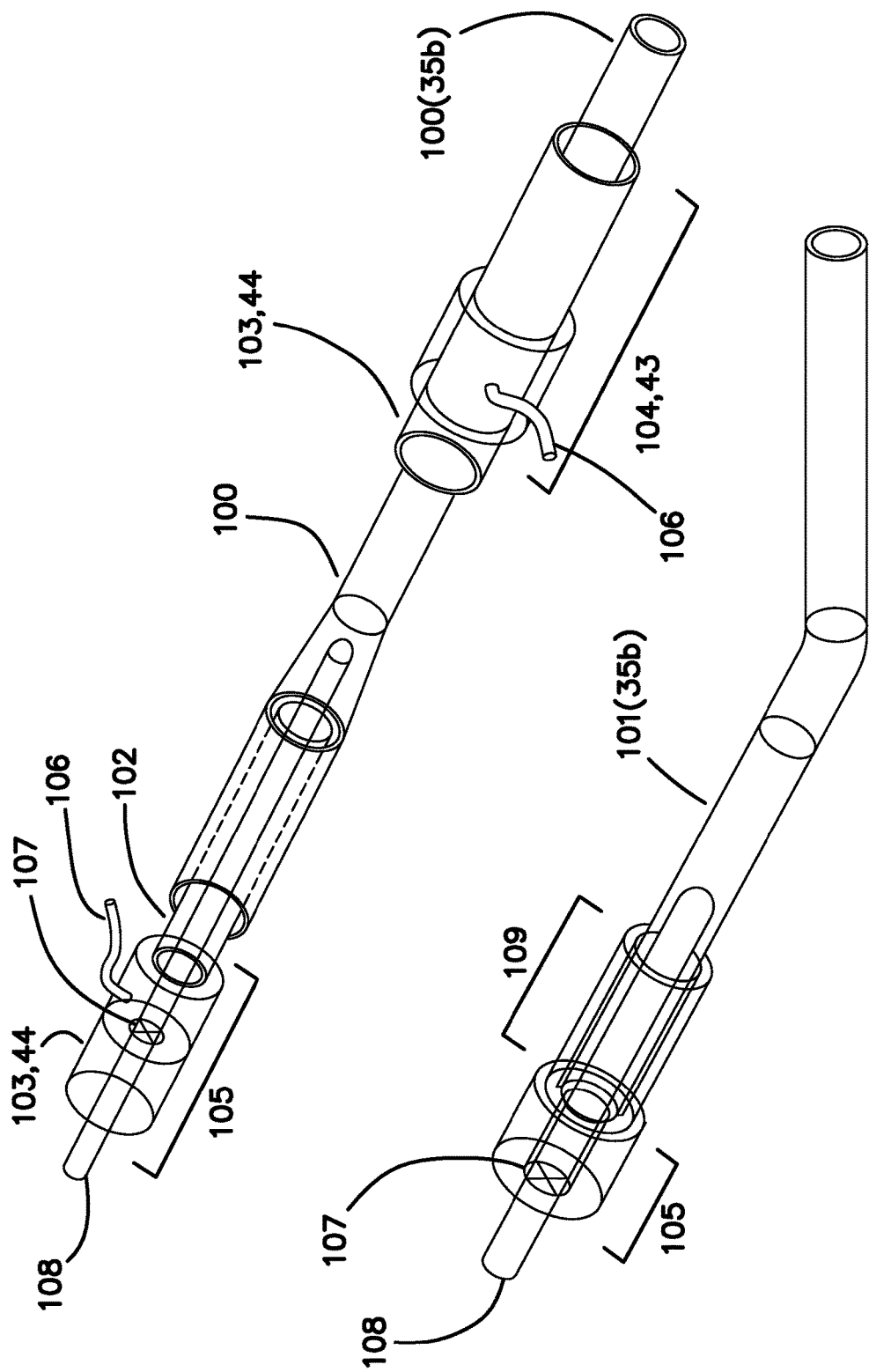
FIG. 8: View of catheter and Hub fusion, and, sheath and Hub fusion.
Figure 9:
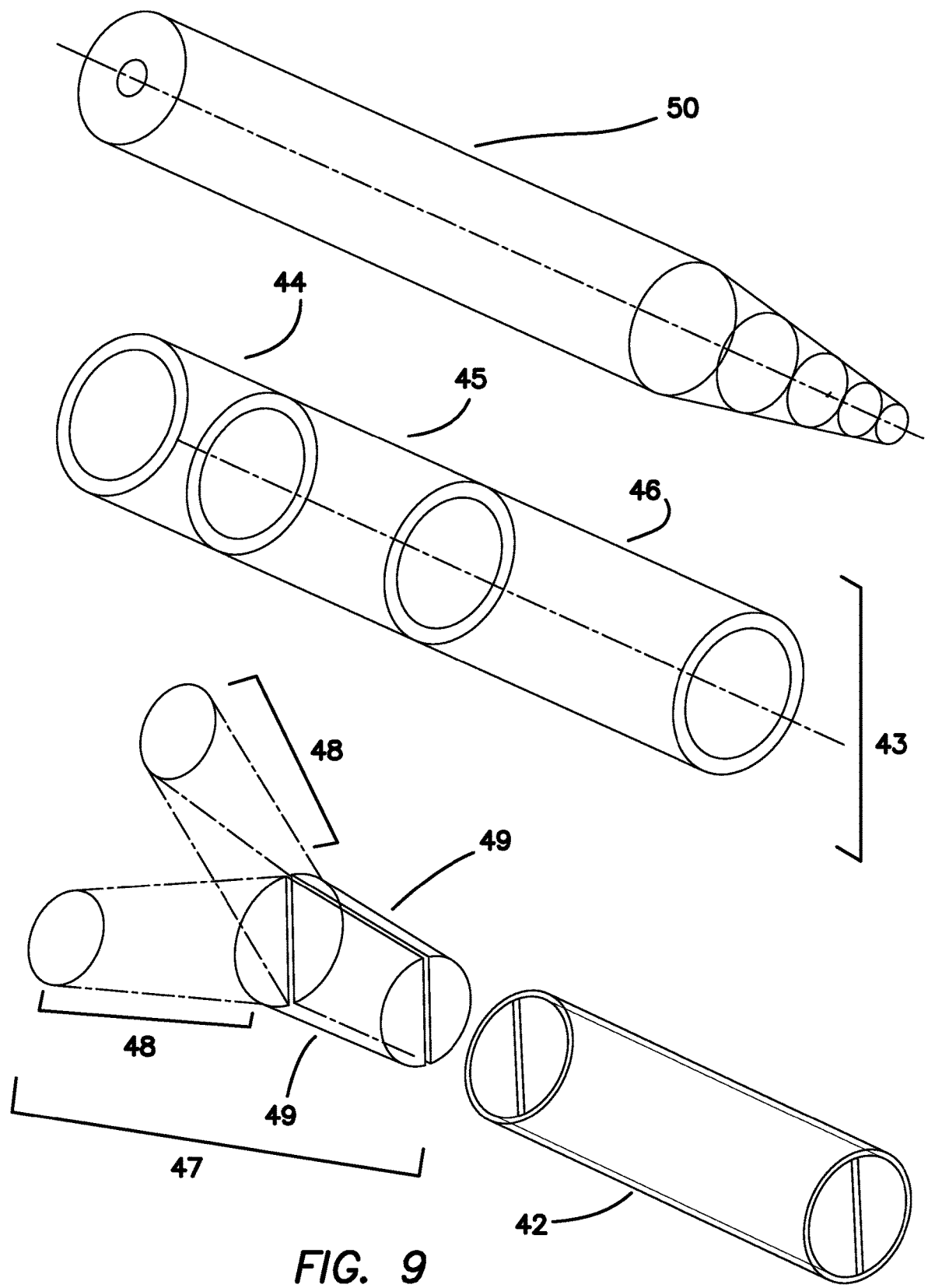
FIG. 9: System integrated vascular introducer sheath.

FIG. 2 presents benefits to the operator of the proposed system. There are nested levels of awareness that are presented to the operator. In the immediate procedure field (16) the operator has control of the patient access site and vascular introduction sheath with one hand in the sterile field (1). The second hand holds the hand grasp (2) and operator interface (8). The hangrasp+operator control interface may be operated with a variety of hand grasp positions, single or dual handed. The smartphone (10) is in the immediate procedural field, although it generally is non sterile and visible, possibly linked to operator control through voice activated commands (e.g., "save that image," "infuse 10 cc saline over 1 second", etc). The operator is simultaneously able to observe and interact with the patient in the usual and customary fashion, which is very important in "point of care" endovascular procedures. Additionally, the unobtrusive addition of the smartphone, which may be laying on the patient's body, may bring an additional layer of information to the operator in the local environment (17). This may include information about the catheter tip derived from a number of catheter tip based sensor types (13), such as blood flow direction, blood pressure, and possible electromagnetic tracking. Electrocardiographic data (14) transduced from the patient could be presented through the smartphone. Imaging data (17) from local ultrasound, fluoroscopy, digital radiography or other local imaging data could be presented on the smartphone screen directly to the operator during the procedure. Furthermore, additional extended networks (18) would be available, including EMR data, PACS imaging data, supply chain data and triage/scheduling data as they are specifically relevant to PICC placement. The system comprises a "smart instrument" toward a new level of best medical practice in PICC delivery at the "point of care" through extreme technological empowerment of the operator.

Overview of Procedure and Device—Operator Advantages

Highly effective patient care is enhanced through the invention. The operator's hand(s) is(are) ready to attend to the compact sterile field (1). A 12 inch (~30 cm) square would be more than sufficient as compared to a 3 ft×6 ft (~100×200 cm) flat, sterile workspace that is required to unfurl typical PICC systems in order to place the guidewire through the catheter prior to insertion and then lay out the catheter prior to insertion. Within or external to the 12 inch square operative sterile field and in a sterile gloved operator hand, the operator interface controller and hand grasp assembly (39) is placed possibly encircling or otherwise fixedly mounted to the sterile enclosed catheter assembly housing (29) which itself is physically mounted on and connected to an external electromagnetic motion control unit (19,20,21,22,23,24,25,26,27,28) that may include a power source 20 in a subunit 22. The rotor translator elements of the electromagnetic motion control unit have mounted magnetically to the catheter (23 mounts to 34, 35a and 35b) and guidewire (27 mounts to 34,36,38) which are inside the sterile enclosure assembly housing (29). If placed in the sterile field, a portion of or the entire operator control interface and hand grasp assembly could be enclosed in a sterile enclosure such as bag or sheath, or, it could be sterilized for each use. This hand grasp (39) gives the operator physical control of sterile contained end drive elements: a catheter (35b), and, a guidewire (38). It could also give the operator control over one or many fluid reservoirs or other actuators (6) that could be coupled to the sterile enclosed catheter assembly to deliver or suction fluid, or perform other tasks. The sterile end drive elements, the catheter (35b) and guidewire (38) are contained within the sterile enclosed catheter assembly (29). The sterile enclosed catheter assembly and operator control interface and hand grasp are mounted to the external electromagnetic motion control unit (19) before the operator dons gloves to enter the sterile field to perform the procedure, in this case of PICC placement. Via the operator interface controller/hand grasp (39) the external electromagnetic motion control unit (19) and sterile enclosed catheter assembly (29) are manipulated as a unit. The operator control interface and hand grasp assembly (39) may be electronically linked (wirelessly or wired) with with a smart phone (10), and, then (wirelessly or wired) electronically linked to the external electromagnetic motion control unit (19). Any combination of linkages is possible. Wired connections could also be utilized imposing a little added inconvenience. There are a variety of mechanical and hybrid haptic feedback that are available to be displayed. In the operator's sterile field and at his or her fingertips, there is (preferably) an optically clear enclosure (30) that allows the spring state of the guidewire to be observed visually and thereby sensed through transmitted motion. The smartphone (10) may provide a visual data display including immediate procedural field (16) data as well as scheduling, EMR and triage data or other extended network data (17). The smartphone (10) could be used to give voice commands to the motion control system (19), fluid reservoir system (6), local area networked tools (13, 14,15) or extended network resources (18).

The basic elements of the EMMT PICC apparatus combine and allow access to nested networks, giving the operator a seamlessly networked experience of procedural efficiency. The first layer of networking involves the basic elements of the apparatus: the external electromagnetic motion control unit (19), the sterile enclosed catheter assembly (29), the operator control interface and hand grasp assembly (39), and, an optional mechanical structural linking member (25) that may bolster the linkage between the operator control interface/hand grasp to (39, 51) to the motion control unit (19). This linking member (25) would have properties of light weight and, optionally, flexibility. In some embodiments, the linking member (25) would not be necessary as the tubular shaft of the sterile enclosed catheter assembly (29) would be of suitable structural characteristics to provide the necessary support alone. The first layer of the system can allow for the user to observe the actual spring state of the catheter and guidewire through an observation window (30) and/or possibly for electromechanical haptic feedback of the motion control system to the cellphone display or to the operator control interface (51). Additional digital equipment can be networked locally through the second layer local network (17) (e.g., bluetooth) allowing for hybrid data to be generated/displayed (eg tracking, stored energy display, telemetry monitoring). The third conceptual network layer is the extended network (18) which can be integrated through GPS/GSM/3G/4G WiFi/internet or other connectivity to systems including EMR, nursing triage, physician ordering, and radiology PACS interfaces, essentially any data that is available via the smartphone hub. The system documents and logs the "time out" among other procedural checks as an example of EMR connectivity supporting the procedural efficiency. The operator's experience is a wealth of very useful and empowering information access toward delivery of the catheter implant. The continuous access to the EMR and extended hospital/operations networks brings additional advantages.

In one preferred embodiment, the invention combines: an electronic, light weight battery (or other electrical source) powered mechanical motion control system (19) for manipulation of principally magnetic nonsterile actuators (23, 27) which link to other manipulators/actuators that control the motion of the end drive elements (35b,38) which are within a sterile enclosure (enclosed tube 29). The magnetic array of the nonsterile, ideally cylindrically shaped (e.g., barrel), magnetic actuators (23, 27) preferably comprises a unipolar configured circular Halbach array in order to generate the maximum and most uniform magnetic field strength within the space, although other magnetic configurations would be acceptable.

The sterile enclosed end drive elements could contain diametrically aligned cylindrical centrally fenestrated magnetic elements (34), possibly diametrically aligned Neodymium fixed magnets, or, ferromagnetic rods which are coupled to sterile enclosed single use catheter (35b), for eventual implant, and single use/recyclable guidewire (38). The catheter and guidewire will have these magnetic actuators (34) incorporated into the sterile enclosed catheter assembly (29), thereby a magnetic or electromagnetic coupling system, eventually connecting end drive elements to the operators supporting hand: sterile catheter assembly (34, 35a, 35b) to external and nonsterile catheter rotor translator (23) and sterile guidewire assembly (34, 36, 38) to external and nonsterile guidewire rotor translator (27). These end drive elements are then linked to an operator control interface and integrated hand grasp (39,51) through a physical structural linkage to the external electromagnetic motion control unit (19) and sterile enclosed catheter assembly (29) and then a magnetic linkage of rotor translators (23,27) through the sterile enclosure (29). Haptic feedback of the rotor translator motors to the operator interface/hand grasp (39, 51) is possible. The operator control interface additionally allows control of optional fluid reservoir/advanced actuator/sensor (6) controllers electronically (with or without physical wires). The advanced actuator/sensor can incorporate sensors such as blood pressure or EKG sensors. The fluid reservoir/advanced actuator/sensor array (6) is also capable of providing haptic feedback to the operator interface/hand grasp. A second visual and auditory operator interface, a smartphone (10), provides access to a broad band telecommunications link (bluetooth and wifi integration) to achieve a display which may be programmed to allow visual or audible haptic feedback (e.g., physical observation of the catheter location, guidewire stored energy, motor energy, blood flow direction, EKG data or combinations of such), and, the smartphone also may link to local (17) and extended (18) data networks and display this data. Thus, the optional smartphone may be used for immediate procedural information regarding the insertion of the endovascular instruments (catheter/guidewire/fluids/advanced actuators/sensors) and it also may provide other data from the extended networks that are generally not immediately relevant to the physical act of instrument operation.

Integration of ultrasound imaging, digital radiographic imaging and/or electromagnetic tracking to improve efficiency and effectiveness of the system is possible for its intended purpose of PICC delivery. The guidewire and/or catheter (38, 35b) may be designed to provide supplemental information through the sterile enclosed catheter assembly via transducers that can be incorporated through advanced assembly techniques and eventually to the smartphone interface (10). The supplemental information may be directly transduced from the patient's bloodstream from the remote location of the catheter or guidewire tip. The supplemental information could include internal and external patient electrical potential readings (electrocardiographic data). Other telemetry could be displayed such as temperature at the guidewire tip. Sensors such as these would help to guide a central venous catheter to its intended location. The use of a supplemental sub system, which is labeled in figures as "fluid reservoir" (6) could be used to extend the capabilities of the system as described. The sub system can include a fluid reservoir and advanced sensor and actuator array. In addition to hydrostatic contact to the guidewire/catheter tip, electrical or optical contact could be made. This sort of contact would enable advanced sensors, which could also be used to deliver treatment, thereby comprising actuators. The actuator could represent a fluid pump system connected to the sterile enclosed catheter assembly. This pump system could administer fluid from the catheter and at its distal open tip (35b) via the fluid reservoir/advanced actuator/sensor array (6). Treatment could also be electrically or optically mediated. This may require that electrical signal and/or fiber optic leads, and, possibly, grounding leads be incorporated into the sterile enclosed catheter assembly (29), which would require special engineering that is within the scope of prior art. Additional electrical or optical connections would need to be designed and integrated into the sterile enclosed catheter (and guidewire) assembly to connect the actuators attached/incorporated into the catheter and/or guidewire (35b,38) to the control system (10) via electrical slip rings and/or fiber optic rotary joints. The smartphone computer system could additionally be utilized to control further subsystems in order to deliver treatments from the catheter and guidewire tips.

The inventive PICC design philosophy is to provide the best "up front" operator experience of any PICC system while minimizing per unit cost. Use of the system naturally translates to improved throughput and system wide gains. The image of a well-trimmed fly fishing rod is an example of the ideal heft and physical form of the device. It is a trusty tool, both sensitive and strong, that is controlled by a skilled operator. This is the design vision that the operator will appreciate. It, the EMMT PICC system, is indeed its own tool.

The sterile set up is easy and compact. First, attention is turned to the smartphone (10) and ordering information is reviewed and the procedural time out checklist is run and documented. Next, attention is turned to the sterile access site which is prepped out and draped, usually a 12" (30 cm) square sterile drape surrounding a 4" (10 cm) sterile prepped skin surface will be easily sufficient. Next, the sterile enclosed catheter assembly (29) containing the eventual implanted catheter (35b) is snapped into position and mounted to the motion control unit (19). This is accomplished via mounts that are fixed (26), linearly translating (24) or with linear translating and coaxial rotational movement (23, 27) relative to the sterile enclosed catheter assembly (29) longitudinal axis. The sterile enclosed catheter assembly (29) may require "through bore mounting" in some of these mounts, or, some mounts may provide a temporary fenestration for slotted fitting of the sterile enclosed catheter assembly shaft. The operator interface and handle assembly (51, 39) is mounted to the sterile enclosed catheter assembly (29) directly or possibly with an additional mechanical support (25). The operator interface handle assembly (51, 29) may be draped with a sterile bag and placed in the sterile field. Next the operator dons gloves and gown and "enters" the sterile field. Using ultrasound, standard Seldinger access [10] is performed and a venous access sheath assembly of special design is placed (43) with an occluding and removable dilator (50). The handheld system comprised of (19) (29) (39) and (25) is then grasped, controlled and fitted to the venous access sheath at a coupling assembly which includes a compression ring (44) when the sheath dilator (50) is removed. In alternative workflows, the sheath assembly (43) and dilator (50) had been placed previously by a first operator, and, that sheath may have been utilized for venous access. Using the operator control interface/hand grasp (39, 51), the catheter (35b) and guidewire (38) are guided into a position that is felt to be satisfactory based on depth and dead reckoning (no guidance is typically the manner of placement). A radiograph can be obtained at this point in any manner that would be convenient. If the catheter is in good position, the guidewire is retracted and the catheter pinned to the skin and removed from the sterile enclosed catheter assembly (29) through a releasable mechanism (see, for example, Embolic coil delivery system with mechanical release mechanism U.S. Pat. No. 7,901,444), and/or it is cut with a blade. A hub is then mounted as to the cut catheter which is now ready for use. The hub mounting procedure is further detailed later in this description.

The operator is able to manipulate the catheter and guide wire independently using one hand through the use of integrated handgrip (39) and possibly by joysticks/actuators of the system's operator interface (51). The system may be supported in part by a gantry or hanging from a tripod mounted boom. Voice control of certain aspects of the system may be available through the cellphone interface (10). The hand guiding the system is also able to sense the physical linkage to the actuation system through directly transmitted vibration from the tip of the guidewire (38), as it is a well-balanced device. The entire system is designed to be light and easily managed in one hand if necessary, and, to provide a tactile sensitivity through its structural form. Operating the system with one hand allows the operator's other hand to be free to control the vascular access site and to operate in other manners that may be desired and advantageous, even possibly operating the first or a second hand held unit simultaneously in a different (not PICC) application of this technology (dual system operation).

Eyes are placed toward the proximal end of the system, at the patient skin access site sheath assembly to system front vent fitting, where a window (30) is positioned that allows the operator to see the guidewire and catheter and visibly obtain a cue about the potential energy stored in the spring of the guidewire/catheter based on how much the catheter is buckling from the centerline. Alternatively, or in addition to a window, the system may include an electronic sensor that measures resistive force and/or deformation of the guidewire and alerts the user. The window (30) may be built into an area where the guide wire (38) and catheter (35b) may be less constrained by the sterile enclosure, and, this window in turn is built into and incorporates a front vent connection fitting (32) such as a luer lock fitting. The smartphone (10) and its display is generally placed near to the window so that the operator's body position and center of focus do not need to change much during the procedure. The smartphone display demonstrates other information and allows integrated use of the EMR throughout the entire procedure (e.g., physician ordering information, triage information, timeout, telemetry, reporting, chest x-ray ordering and other features).

In some embodiments, the motion control system and sterile enclosed end drive elements may be fitted to the introducer sheath and then secured to the patient as well as a gantry mounted to the patient in some manner, and, then the drive mechanism of the system may operate via its own onboard algorithm. It may also be teleoperated fully or in part by a remote operator (12).

The system may deliver best performance through use of an integrated vascular introducer sheath assembly. To understand this, one must understand the geometrical and structural concept of "linear constrainment" of guidewires (and, sometimes, catheters). A key point to understand regarding "linear constrainment" is that, in general, the specific tool of an endovascular guidewire achieves its best physical performance characteristics when it is allowed to extend fully in a straight line. In any position aside from the linear state, the guidewire or catheter has some mechanical stored spring energy and increased friction and physical binding force that results in the net effect of poor handling that is often characterized by endovascular medical specialists as "poor pushability and poor trackability." To be free of any such superimposed system aberrations, the guidewire and catheter should be held as close as possible to a physical straight line configuration. The system derives its elemental form through embodiment of a linear constrained system that may remain flexible, for example a straight 1 meter length of medical grade plastic tube as a constrainment guide. A spiral tube constrainment guide could have advantages in portability of form, however, there would be costs in ultimate performance of the system.

Linear constrainment is further divided into two basic forms: (1) the constrainment force and tip pushability and pullability that is provided to a guidewire or catheter by tight cylindrical constrainment alone; and (2) the directional and constrainment force provided to a tubular structure (catheter) by a centrally passing guidewire (the "rail"). Typically for a PICC, the guidewire and catheter are between 50 cm and 2 m, preferably between 75 cm and 150 cm; in some embodiments the guidewire is at least 30% longer than the catheter, in some embodiments about twice as long as the catheter.

Linear constrainment of a guidewire is useful because when a well constrained guidewire encounters a feature at its advancing tip that generates resistance at the tip, that resistance can be transmitted through the rigid guidewire and thereby sensed at the back end of the wire. This sensitivity, which is a feature of the rigid metal in its linear state, can be damped or completely lost into stored spring energy within a buckled guidewire or catheter/guidewire system Minimizing buckling maximizes ability to sense the guidewire tip. Indeed, constrainment gives a catheter its ability to be moved precisely at the tip. Thus, elimination of the external body guidewire buckling is advantageous. For this reason, constrainment of a bare catheter without a hub is the best solution to maximize performance of a catheter delivery system. It can be seen that a hub such as Luer lock would increase the diameter requirement of the constrainment guide, and, thereby, would increase the buckling potential of the guidewire or catheter within the constrainment system, impeding its function. And, for this reason a hub must be mounted to the catheter delivered by the system in its most functional design, after the catheter has been removed from the system's constrainment. Thus, the system sheath should have a design to aid in catheter+hub fusion. This will be discussed further in the following sub section titled "System integrated vascular introducer sheath detail."

Sterile Enclosed Catheter/Guidewire Actuation Subcomponents

The electromechanical actuation system subcomponents are important for effective functionality of the EMMT PICC system. There are four major design features regarding the EMMT PICC electromagnetic actuation subsystem to consider closely, first, magnetic force generation and its optimization, second, hydrostatic force management, third, end drive element releasability, and, fourth, linear constrainment/support.

For example, in the PICC designed system with a single catheter that may rotate and translate (although rotation is not required in every instance) and a single guidewire that may rotate and translate (although rotation of the wire is not required in every instance), it will be important to maximize the magnetic force of alignment between the external catheter rotor translator (23) and its internal sterile enclosed end drive catheter electromagnetic actuator sub assembly (34, 35a, 35b), and, similarly, the external guidewire rotor translator (27) and its internal, sterile enclosed end drive guidewire electromagnetic actuator sub assembly (34,36,38). Stated another way, the end drive electromagnetic actuation elements are magnetically coupled for maneuverability through the constraining internally sterile enclosure assembly (29) to the external rotor translators which are mechanically operated by an external motion control system mounted to the external surface of the sterile enclosed catheter assembly (29) via a mounting system. Fixed magnet(s) or electromagnets) of the external rotor translators (23, 27) are coupled to fixed magnet(s) or ferromagnetic aligning and ideally barrel shaped structure(s) (34) within the enclosure which are braced against the inner surface of the sterile enclosure and simultaneously coupled to the end drive element (a catheter (35b) or guidewire (38)) through a low hydrostatic profile linkage (35a or 36)). Use of single magnet systems would be simplest. However, it is important to point out that a simple single dipole magnet coupling at a single point on the circumference of the rotational path of the tubular enclosure may result in a relative increase in contact pad force at the coupling alignment point and relative increase in frictional losses with motion compared with other arrangements of magnets. An encircling or near encircling diametrically aligned ring magnet or encircling dipole magnet array would have significant advantages to a single magnetic coupling point. Furthermore, encircling magnetic arrays can be fashioned in order to focus the magnetic flux closely into the central portion of the ring, as in a circular Halbach magnetic array. Fixed magnetic barrel shaped circular Halbach arrays with unipolar diametrically aligned magnetic fields would be ideal. Either of these types of arrangements for the external rotor translator (23 or 27) magnet would have significant advantages in end drive element force of coupling: (1) the wall contact forces of friction would essentially cancel out leaving a net alignment force and minimized friction force, and, (2) the magnetic field flux outside of a Halbach rotor translator and thus interference with the external environment would be absolutely minimized. Fixed magnets, in a Halbach arrangement, would be the simplest alternative for the outer (23, 27) or inner (34) magnetic elements, however, in the case of the external rotor translator (23 or 27) magnetic element, electromagnets, even superconducting electromagnets could be used to increase the amount of force applied to the sterile enclosed end drive actuator elements (34, 35a, 35b, 36, 38). The rotor translators (23, 27) would themselves be actuated externally through physical attachment to an electronic mechanical supporting structure with possible linearly fixed (26) and linearly translating (24) constrainment rings comprising the external electromagnetic motion control system. Indeed, so called "frameless" electromagnetic arrays could be utilized as rotor translators (23, 27) so as to have no moving mechanical parts involved in the rotational actuation of the end drive elements within the constraining sterile enclosed catheter assembly, but, a mechanical means of moving the external rotor translator magnets through their useful orbits would likely use much less power and require much less electrical apparatus and complexity. Creating a C shaped circular Halbach array for the external rotor translator magnet element (23 or 27) would have advantages in that the sterile enclosed catheter assembly could be mounted through the perforation/gap in the ring (through the gap in the "C") quickly and easily at any point along the length of the sterile enclosed catheter assembly. This would allow a quick release manner that a solid ring magnet array would not allow. However, a solid ring through mounting over the distal end cap and then shaft of the sterile enclosed catheter assembly (29) is certainly reasonable as an approach. One slight inconvenience with this mounting is that it would require temporary removal of any fluid reservoir and advanced sensor and actuator (6) associated tubing and leads that may be connected prior to mounting. In the case of fluid connection, this is not likely to be a problem as flushing air from the system via coupling to a fluid reservoir (6) could occur just as easily after mounting the sterile enclosed catheter assembly (29) to the external electromagnetic motion control system (19). In addition, a fluid access portal (31) is incorporated into the sterile enclosure. The sterile enclosed catheter assembly (29) could simply be placed coaxially through the bore of the two (or one or greater number) of partially retracted external rotor translator assemblies (23, 27) and any number and types of supporting mounts (24,26) prior to attachment to any fluid reservoirs/advanced actuators/advanced sensors (6) that may be used.

As the rotor translators provide the linear translation component of their force to the end drive elements of the catheter (35b) and guidewire (38) there is a potential to exert a coupled hydrostatic pressure on the fluid column suspended within the sterile enclosed catheter assembly, similar to a hypodermic syringe. This could result in a net outward pressure force or inward suction force at the front vent hub opening (32) of the sterile enclosed catheter assembly if the internal catheter (35b) or guidewire (38) was being pushed forward or retracted. The motion of rotation would probably have less of an effect on the hydrostatic pressure generation, unless the end drive magnetic actuator was purposefully designed to generate pressure differential through rotation, such as a propeller or turbine impeller form, which may have utility in some instances. The hydrostatic force related to pushing or pulling the catheter and guidewire through the sterile enclosure with regard to PICC applications would have to be controlled to maintain the purest balance and functionality of the system in its coupling to a fluid filled artery or vein, for example. Continuous positive pressure flushing from a connected fluid reservoir (6) is a very good option. Attention to minimize the cross sectional profile of the end sterile enclosed magnetic drive element/electromagnetic actuator (34) is important in minimizing the net force that these elements place on the fluid column contained in the sterile enclosed catheter assembly. Integrated design of perforations of the inner sterile enclosed magnetic actuation element is important to consider. This could involve placement of an internal ferromagnetic rod, a diametrically aligned cylindrical fixed magnet, or, internally placed circular Halbach array, any of which could be engineered to support large central or otherwise aligned perforations or tubular windows with little loss in capability for magnetic force generation. To some degree, the internal electromagnetic actuator element should mimic the form of the external catheter/guidewire rotor translator, but, with a smaller outer diameter, ease of sterilization, and, a low cost so as to be disposable after a single use. A diametrically aligned cylindrical fixed magnet may be optimal as it has a large central fenestration and can be closely approximated to the external magnetic rotor translators. This could be embedded into plastic in order to develop a supporting structure for the end drive elements. In the case of coupling to the catheter end drive element, a cylindrical sieve plate mount (35a) from the enclosed magnetic actuator element (34) to the end drive catheter (35b) could also be employed in order to help maintain neutral hydrostatic pressure between the inner lumen and outer space of the catheter in front of the magnetic actuator element (34) which would be braced against the inner wall of the sterile enclosed catheter assembly (29). In some embodiments, the catheter is sealed with an o-ring at its distal exit, at the front vent (32) which could lead to hydrostatic pressure generation along the length of the catheter, outside of the catheter, within the sterile enclosed catheter assembly (29). The cylindrical sieve plate mount (35a) would solve this potential fluid management problem. The sterile enclosed magnetic drive element/electromagnetic actuator (34) can be braced within the outer tubular constrainment guide via close tolerance fitting, thus it preferably has a cylindrical form to fill the inner lumen of the tube. It would be possible to use hydrophilic coatings in order to further minimize the friction between the inner wall of the sterile enclosed catheter assembly tubular shaft and the magnetic drive element/electromagnetic actuator (34). If significant hydrostatic force generation was still present following engineering optimization, additional attention could be placed to the attached fluid reservoir (6) and its controllers in optimization of the system with regard to hydrostatic pressure generation. For example, (6) could be programmed to open the chamber with advancement and close the fluid chamber with retraction. This would have the net effect of introduction of fluid on advancement and static fluid column with increased drag on the motion in retraction. This would be an acceptable arrangement as the sterile enclosed catheter assembly would remain "bloodless" and there would be little loss in functionality. A continuous positive pressure at (6) would also work and would be simpler to achieve. Furthermore, there could be many arrangements and methods to deliver fluid via (6) including liquid medication administration and even CO2 gas for related angiography methods. Having perforated or low hydrostatic profile magnetic drive elements/electromagnetic actuators (34) within the sterile enclosed catheter assembly (29) is important to the final functionality of the system. Preferably, components are porous and/or block less than 90%, more preferably less than 50% of the cross-section (perpendicular to flow) of the enclosed tube.

Mounting the magnetic drive element/electromagnetic actuator (34) to a guidewire (38) is a fundamentally different geometric arrangement relative to mounting of a catheter (35b) with respect to hydrostatic force generation. Again, a perforated structure will be desired to minimize hydrostatic force generation. The larger the net cross section of the fenestration void area, the less the hydrostatic force generated by translational motion within the enclosing tube of the sterile enclosed catheter assembly. A cross braced annular sieve mount (36) is a desirable form of the coupling spanning a cylindrical sterile enclosed Halbach array actuator, for example, to the central or off center placed guidewire end drive element (38). Alternatively, a simple single or dual post mount radially and centrally projecting from a cylindrical magnetic drive element/electromagnetic actuator could be used rather than a cross braced array.

Along with hydrostatic force generation, releasability of the magnetic drive elements/electromagnetic actuators from their respective end drive elements of the catheter and guidewire should be considered. There is always the magnetic releasability which is inherent in the system. The catheter and guidewire are held in position by magnetic force that may be overcome by pulling or pushing against the support tube of the sterile enclosed catheter assembly. Additional mechanical and/or electric and/or electromagnetic release actuation may be utilized further. As the most simplistic method, a designed "breakaway" release is possible, which would require an engineered fracture point in the linkage holding the catheter (35b) to the catheter electromagnetic actuator (34) and this fracture point could involve any portion of the sieve mount (35a) attachment or some specially designed portion of the catheter (35b) itself. The catheter could also just be cut by a scissors at any point along its length once it was pushed out of the sterile enclosed catheter assembly (29). Still a second point of breakaway releasability would likely have utility as a fail safe. In the case of the guidewire (38), it could be fractured at a structural score location proximal to the guidewire electromagnetic actuator and annular sieve (34, 36) or, it could also be cut by a scissors or shear from the actuator assembly (34, 36). More complex actuated release of the elements is also possible. There are several methods for embolization coil and guidewire release that are known to those versed in the art, and, any of these release methods could be used in a modification in order to serve the purpose at hand. (Embolic coil delivery system with mechanical release mechanism U.S. Pat. No. 7,901,444, for an example of rapid exchange over the wire catheter with breakaway feature see WO 1993011822). Additional electrical, mechanical or magnetic actuators would have to be modified for use with the system.

Releasability of the catheter (35b, 42) would eventually be required in order to create a free catheter implant to be left in place within a patient, as is the goal of the PICC procedure. The guidewire (38) would not need to be separated for catheter implant creation, and, in some cases it would be better to keep the guidewire within the sterile enclosure for ease of disposal and environmental protection from blood contamination. To free the catheter and guidewire completely from the motion control system and the sterile enclosure assembly would allow the system to derive a level of flexibility toward the next steps that are typical and essential to a host of endovascular procedures. For example, diagnostic aortogram and superior mesenteric access sheath placement could be performed with a modified system, and, the released catheter tube, a superior mesenteric access sheath possibly with a hemostatic valve and sideport access fused, could be used in the further steps of a procedure that relies on work performed through a celiac access sheath, such as internally bleeding vessel embolization. These additional procedural steps can be thought of as building onto a PICC placement procedure, which is similar to selective vascular introducer sheath placement. Arteriography would require injection of intravenous contrast for digital subtraction fluoroscopic x ray angiography. Thus, the invention includes use of the inventive devices and methods in these applications. The contrast administration through a catheter that is not separated from the delivery system would rely on fluid administration via a fluid reservoir actuation mechanism (6) that is connected via tubing to the lumen of the sterile enclosure and eventually to the tip of the catheter (35b). There are prior art addressing such mechanisms (Medical fluid injection system U.S. Pat. No. 20140039310). Modifications of these techniques could be applied to the current system with a key integration into the operator control interface and eventually the catheter tip. Additional design features related to (1) hydrostatic seal points and (2) fluid continuity with the catheter lumen would be required. These hydrostatic seal points could be utilized to isolate lumen(s) of the contained catheter(s) element relative to the external fluid reservoir, and, most straightforwardly, the entire housing could have an o ring seal at its front vent/luer lock (32) fitting closely around the outer diameter of the catheter (35b). This would provide fluid continuity of the catheter lumen at the catheter tip to the fluid reservoir (6). Additionally, in particular with noted placement of the previously described sieve mount holding the catheter to its electromagnetic actuator, the front vent (32) associated o ring seal could be loosened which would have the effect of allowing fluid to escape around the catheter from the sterile enclosure into the vascular introducer sheath, which would have great utility in certain circumstances allowing fluid administration through the delivery sheath as well as the catheter tip. The o ring seal could be adjustable so as to be switched between delivering fluid from the catheter tip or the catheter tip and introducer sheath tip.

External Electromagnetic Motion Control System

The entire system is designed to be a handheld device or hand supported and guided device. Its weight could be supported in part by a stand/mount, or, on the patient's bed as is typical of other catheter and guidewire systems that are used in angiographic procedures. End drive elements (34, 35a, 35b, 36, 38) can be manipulated via an operator interface that is incorporated into a handle (39) for additional support/guiding of the entire device. The motion control system (19) can be coupled to the operator interface handle by means of the actual sterile enclosure tubular shaft (proximal portion of 29) and possibly with an additional supporting member (40) that bridges the operator interface handle (39) to the motion control system (19). The motion control system (19) is comprised of a power supply (20) that is ideally entirely portable and onboard, a battery. Wired power from an external source could be used as well. The motion control system also incorporates a structural support for a gantry approximating the length of the sterile enclosed catheter and guidewire elements. Ideally, the length would accommodate possible extension of a bare guidewire through a catheter to be deployed to a target length for the catheter and then advancement of the catheter over the extended guidewire to the target. This could result in a tubular enclosure that is twice the length of the eventual implant, assuming a first guidewire deployment to target followed by guidewire deployment over that catheter. For example, for a 60 cm PICC, a guidewire of length greater than 120 cm would allow bare advancement of the guidewire alone to a target 60 cm or less from the system front vent (32). Over this bare wire extending 60 cm from the front vent, the catheter (60 cm) could be advanced, covering the external guidewire and exposing the sterile enclosed portion of the guidewire. The guidewire could then be retracted and the catheter released or cut for the implant. However, it is usually the case that a catheter is advanced simultaneously with an internally passing guidewire, such that the bare guidewire is exposed only 5 to 10 cm beyond the catheter tip. In this case, the entire motion control system could be considerably shorter, for example 70 cm rather than 120 cm. Indeed, the length of the entire system could be equal to that of the eventual implant, for example 60 cm, if the guidewire was simply an internal supportive structure to aid delivery of the catheter implant, a stylette. For purposes of catheter and guidewire manipulation techniques, it is better to have some bare exposed guidewire in front of a catheter to allow more maneuverability.

The system support gantry would hold one or more rotor translator magnetic elements (23, 27). These elements can undergo linear movements along the length of the sterile enclosure and shaft of the motion control system 19, and, they can undergo rotational movements around the central axis of the elongated tubular sterile enclosure. This motion would likely be accomplished through a system of gears, worm screws and possibly belts and pulleys linked to electric motors that are involved in the mechanical linkage of the rotor translator magnetic elements (23, 27) to the supporting structure of the external electromagnetic motion control system (19). It would have an onboard microcomputer and communication system (21). There are a variety of motor and linkage configurations which could be engineered to maximize functionality and minimize cost and complexity.

The electromagnetic motion control system (19) would be designed to mount fixedly to the sterile enclosed catheter/guidewire assembly (29). The mounting process would involve disposal of the tubular shaft of the sterile enclosure coaxially through the centers of the external rotor translator elements (23, 27) and possible other constrainment guides (24 which moves linearly, 26 which is fixed in place). As stated before, this could be achieved by passing the distal end of the sterile enclosed catheter/guidewire assembly through the rotor translator bore, or, by creating a window for passage of the sterile enclosure through the annulus of the rotor translator. Either manner is acceptable. Additional nonmagnetic coaxial guides for the sterile enclosure could provide additional support as needed (24, 26).

The sterile enclosed catheter assembly (29) locks to the electromagnetic motion control system (19) gantry to provide rigid attachment without rotation of the elements relative to one another. An optional support member (25) linking the proximal sterile enclosed catheter/guidewire assembly to the operator interface handle is possible and may have benefits.

The entire sterile enclosed system can be coupled via tubing to a fluid reservoir system (6) for control of fluid flow at the proximal end of a catheter. There may be a vent attachment point of the sterile enclosed catheter system (29) to the external fluid reservoir at the distal end of (29) where a rear vent and coupling fitting (33) can be located. Additional venting(s) can be placed in the middle or anywhere along the length of the enclosure (31). A front vent and attachment fitting (30) is on the proximal end. Simple control of fluid pressure at the end of the catheter would be useful in extended applications of the system.

Operator Interface/Hand Grasp Support

The operator control interface and hand grasp support sub assembly (51, 39) is designed to give the user, ideally, one handed control of the catheter and guidewire. This hand provides physical support and control over the orientation of the sterile enclosed catheter assembly (29), the electromagnetic motion control system (19) attached fixedly to it, and, the operator interface hand grasp (39) and possible support shaft (25) that comprise the major elements of the system. Fluid pressure control is allowed through the operator interface which is connected to the fluid reservoir (6) controller. The operator interface and hand grasp are placed at the proximal side of the system in order to place the operator at the traditional endovascular operating position, with one hand able to control the vascular access site and attend to the requirements of hemostasis and general endovascular procedural work required and typically performed at this location. The operator interface itself may be controlled by one or more finger joysticks (51) or possibly by a combination of switches, voice commands, joysticks and other manners enabled through wireless or wired linkage to a smartphone (10). The operator interface could alternatively be controlled remotely through a local or extended area network (11,12) by a second operator allowing the first operator to attend to other procedural issues.

Catheter to Hub Coupling Components and Discussion of Advanced Applications

In order to deliver a useful PICC implant, the delivered catheter requires a functional hub termination at its distal end to be used for medical treatment by infusion or sampling. An ability to create a hub at any position along a catheter "on the fly" would have particular advantages in the application application to PICC, because each patient anatomy and access site location has a particular optimal catheter length. The PICC with an "on the fly" hub creation could be customized on a per unit basis with a luer lock fitting at the skin level for use. In the case of alternative catheter applications as conduits for interventional radiology/endovascular procedures, a hub with two elements (1) a hydrostatic pressure infusion side port, and, (2) a hemostatic introduction port for a guidewire or other tool. The most basic hub termination is a luer lock fitting, which can be capped with an appropriate additional fitting, or, attached to medical tubing or syringes as the luer fitting is essentially an industry standard fitting.

More complex hub terminators to be fitted to catheter tubes are generally not used in PICC but instead for interventional radiology procedures. A very useful hub includes an often T-shaped or Y-shaped ensemble of (1) a hydrostatic pressure infusion side port, and, (2) a hemostatic introduction port for a guidewire or other tool. This type of arrangement allows for external hydrostatic pressure infusion or sampling while the main lumen is partially occupied by a tool such as a guidewire entering the catheter lumen at a hemostatic (atmospheric sealing "dripless" valve) with tip displaced into the patient.

An ideal pre fabricated and non customizable length catheter+hub for use in the proposed invention would be very "low profile," essentially having an outer diameter very similar or slightly larger than the diameter of the implanted catheter. A hollow metal screw tipped hypotube bonded to the silastic catheter would be an example. A typical bulky luer lock hub could then be attached easily by threaded fitting following catheter deployment. PICC silastic catheter material is usually of outer diameter 5F, which is less than 2 mm (1.67 mm). The diameter of a male luer fitting, which is the universal medical tubing adaptor, is about 45 mm. Therefore, it would be useful to fuse a luer lock type hub to a catheter following its removal from the sterile enclosed catheter assembly of the proposed invention, in order to maximize the pushability of the catheter while it was disposed within the sterile enclosed catheter assembly. There would be less buckling and shortening of the catheter and guidewire if they were constrained closely. Methods to achieve catheter to hub fusion in (1) flexible type catheters (100) (typical PICC), and, in contrast, (2) rigid plastic PMMA catheters (101) (access sheaths, diagnostic angiographic catheters) are briefly described. Furthermore, a hub including a hemostatic valve and a side port fluid access is proposed for extended applications beyond PICC.

In the first case, where the deployed catheter is a flexible, compliant (e.g., silastic) catheter, the catheter would have a property of increasing its diameter by stretching in order to accommodate an internally passing, rigid tubular structure/hypotube (102) with or without external etching, external diameter variability (flared or beveled shape) or scoring barbs. The catheter could additionally be interposed between a rigid internal hypotube and an external compression ring (103), in order to create a fitting of the catheter tube to a large diameter bulky hub with a high pressure seal capability (900 psi). This sort of fitting would also be very durable. In order to be most useful to the PICC application and to the other extended applications, the compression ring (103) could be mounted to the initial access sheath (104) gaining first introduction to the vessel. This can be a removable and very low profile "peel away sheath." This would allow a very easy transition from bare catheter to catheter+hub construct as the encircling compression ring (103) would already be in position encircling the catheter/implant at its initial introduction, and, the catheter and compression ring would be ready and in close position to accept the internal fitting rigid hypotube (102) and bulky external hub (105) component. In this case of flexible tubing (100), a bare or released catheter would be cut a few cm from the insertion point access sheath, a hypotube (102)+bulky hub (105) construct would be coaxially pushed into the catheter lumen, and, this construct could be pushed into the access sheath hub associated breakaway compression ring (105). Force could be exerted to the separated compression ring (105) alone to make the fitting, or, the compression ring (105) could be pressed into position while attached to the vascular introducer sheath (104), which may provide additional grasping support structure. In this way, the hub could be created with few physical steps and minimal risk for inadvertent catheter dislodgement and free embolization into the patient's bloodstream. Additionally, bulky hub (105) modifications could include side port access tubes (106) and hemostatic valves (107) in order to create an introducer sheath arrangement with ability to accept a coaxial instrument (catheter and/or guidewire) while still having a fluid "side port" for administration of fluid or fluid suction. This could allow for creation of customizable length sheaths (a sheath having a sideport and hemostatic valve with or without luer adaptors where a catheter would only have a luer lock port) as well as customizable length catheters (typically only having a luer adaptor fitting at the distal end).

In the case of typical vascular introducer sheaths currently in use for endovascular procedures, these are generally fabricated from more rigid PMMA material or braided composite material rather than compliant silastic material typical of PICC. Thus, the sheath tubing materials currently in wide use would generally not be capable of stretching over a hypotube of the same diameter to form a seal as previously described. In this case, hub fusion would be more challenging. One method to overcome this challenge would involve a hub fusion method that is disclosed as follows and in the accompanying drawings. First, a hemostatic valve with or without a sideport or luer fitting (105) assembly would be held on an internally passing obturator (108) of outer diameter matching the inner diameter of the tubular introducer sheath conduit to which the hub or hemostatic valve is to be fused. The hub would have a proximal end sleeve (109) that could accommodate the sheath tube internally coaxially, of slightly larger diameter than the tubular sheath (101) conduit outer diameter. The hub (105) would eventually decrease abruptly in diameter to a diameter smaller than the sheath tubing, which would stop the internal progression of the catheter bracing it against the hub (105) and providing a preliminary seal. With the tubular sheath (101) braced in this manner against the hub and the lumen of both elements internally occluded and bridged by the obturator, a bonding agent could be applied to fill the void between the sleeve and the internally placed sheath creating a hemostatic high pressure bond. The bonding agent could be applied in a variety of manners, but, engineering its delivery into the hub components through microfluidic channels is one method.

Another method would be use of the obturator (108) to place the bonding agent via the inner lumen of the composite structure. The obturator would protect the lumen from embolization or occlusion by the bonding agent. Ideally, the bonding agent would be unable to bond to the obturator, or, fittings could be designed to protect the obturator from the bonding agent. The bonding agent would have to be of suitable viscosity to form a gapless bond through flowing and cohesion without air gaps/filling voids. A number of bonding agents are currently in use that would meet these specifications.

In another embodiment of a system that would not require catheter/sheath to hub fusion, the catheter and a larger diameter bulky luer fitting on the distal end of the catheter could be pre-fused and mounted within a suitably large diameter tubular housing of a sterile enclosed catheter assembly. An array of internal spacer disks or a metallic spring supports (not pictured) could be placed within the sterile enclosure and alongside the length of the catheter in order to provide internal constrainment of the catheter tube against the inner wall of the sterile enclosure proximal to the bulky hub, thereby constraining the catheter where there would be potential for buckling Fashioning the internal spacer disk array or metallic spring(s) to accommodate the catheter closely fitting within a "notch" along the outer peripheral surface of the spacer disk would allow the disks to be easily released from the catheter when they were freed from the sterile enclosure through a port in the distal end of the sterile enclosure. This sort of internal disk/spring spacer system would provide a way to maintain pushability of a narrow catheter+larger diameter hub for use in the electromagnetic actuation of the sterile enclosed system. The disks or metal spring, being non-encircling to the catheter implant, could be easily removed from the implant when it was removed entirely from its tubular enclosure. The front vent and catheter seal could be left in position around the catheter with little increase in hub bulk and no functional detriment.

Single and Multi Lumen Catheters

Conceptually, we have generally considered the catheter (35b) to be single lumen to this point. Next, we will consider the system functioning in the case of carrying a dual lumen catheter (42). A detailed diagram demonstrates how a catheter of this configuration may appear in cross section. The guidewire would pass only through a single lumen of the catheter. Otherwise, to this point, the system would perform nearly identically. In the next section, we consider hub fusion to a dual lumen catheter (42), which presents important subtle modifications of design to the hub fusion that should be considered to provide a dual lumen PICC implant.

System Integrated Vascular Introducer Sheath Detail

The EMMT PICC system, comprised of the external electromagnetic motion control system (19), the sterile enclosed catheter assembly (29), operator control interface and hand grasp (39), a possible supplementary mechanical linkage of (39) to (19) and possibly (29) and the smartphone device (10), is designed to deliver an implant which is part of the catheter assembly (34,35a,35b) stored in the sterile enclosed catheter assembly (29) into the body of the patient to serve as a central venous catheter. This generally requires passage through a previously placed vascular introducer sheath bridging the external environment to the endovascular endoluminal environment. The sheath is typically placed via the Seldinger method [10] and modifications of this technique. The Seldinger access method begins with the percutaneous introduction of a needle into a tubular vessel or hollow viscus organ preferably via a "single wall" puncture of the tubular structure via the needle with the tip placed inside the lumen of the hollow viscus organ. The percutaneous needle access can be aided by imaging such as ultrasound or fluorscopy. The needle placement is then followed by advancement through this needle of a supporting guidewire through the needle extending some distance of typically 5-30 cm into the tubular lumen. The guidewire is typically 0.038, 0.035 or 0.018 in diameter. The needle is then removed completely from the vessel and removed from the back of the guidewire leaving the guidewire bridging the external environment, passing through the skin and subcutaneous tissues and entering the lumen of the tubular organ.

Over this supporting guidewire, a tubular "access sheath" for secondary tool coaxial placement is eventually advanced, possibly following skin incision and serial dilation of the arterial or venous puncture zone tract along the guidewire using sequentially larger and larger diameter dilators in order to minimize the trauma to the arterial or vascular wall. The vascular introduction sheath (43) is eventually passed over this guidewire with a mated and tapered space occupying internal dilator (50). The dilator (50) is eventually removed and the hollow, tubular sheath (46) that is left in place provides a conduit for entry and reentry into the tubular viscus lumen. The sheath is usually made of medical plastic and may often have a "break away" or "peel away" capability that allows the sheath to be removed while leaving in place a centrally passing second catheter or sheath passing through the first "peel away sheath." A hemostatic valve (107) is often integrated into a typical vascular introducer sheath. This is the usual method for so-called "access sheath placement" for interventional radiology/endovascular surgical procedures. It is important to note that the system, in the case of dual lumen PICC, delivers a portion of flexible medical endovascular catheter tubing (35b) which is releasable from the electromagnetic actuator and the magnetic elements of the sterile enclosed catheter assembly (29). The catheter (35b) may be trimmed with the guidewire retracted completely back into the sterile enclosed catheter assembly (29), for example, by an 11 blade scalpel or scissors. The catheter (35b) must eventually be fitted to a luer lock retention hub carrying and mounting one or more lumens (47). The two lumen example is further detailed in following descriptions as an example, although it is technically more challenging than would be for a single lumen catheter.

The sheath designed for integration with the current invention (43) through which the bare catheter (35b, 42) is deployed is a design that has advantages specifically when utilized with the EMMT PICC system as described, particularly in that it allows mounting of the free catheter (35b,42) to an eventual hub construct through the addition of a separate piece carrying, in the case of a dual lumen catheter, 2 additional luer lock lumens with luer lock adaptors as well (47). The mounting of (47) to (42 or 35b similarly) occurs through two separate and internally isolated rigid hypotubes (49) likely to be constructed of stainless steel or plastic that may be externally fused. These hypo tubes may be flared proximally or distally so that pressing (42) over (49) provides some elastic constrainment of the bare dual lumen catheter (42) to the hub (47). Directional friction etching may also be used. However, this level of constrainment is likely to be insufficient. The dreaded complication of embolization of the free catheter into the body must be avoided completely, requiring a durable and completely permanent fitting. Therefore, the sheath (43) conduit tube has key features to be noted.

First, a portion of the sheath may be separable so as to "peel away" (46) over the implanted catheter (35b,42) separated from the remaining magnetically charged and perforated portions of the catheter assembly (34, 35a) that remain attached to the sterile enclosed catheter assembly unit (29) with minimal mechanical disruption. This "peel away" method and functionality is well known to practitioners of the art of interventional radiology. It is typical that most vascular introducer sheaths for PICC and other implanted central lines "peel away" completely and are completely removed, being temporary access conduits.

Second, a portion, at least, of the sheath will not peel away (44, 45) from around the eventual implant catheter, for example a dual lumen catheter (42) or a single lumen catheter (35b). These left in place encircling member(s) (44,45) may serve additional functions when combined with the catheter (35b,42) and a hub element (47) which is intended to be eventually fixedly fused to the catheter externally to serve as an external connector. These functions of the left in place portions of the introducer sheath (44, 45) principally involve securing the fusion of the catheter (35b, 42) to the hub element (47) and then securing the hub and catheter assembly to the skin. In this case of a dual lumen hub, coupling of a variety of medical tubes for fluid sampling and administration is accomplished usually through a system of female and male luer lock fittings. An important and useful feature is the fusion aiding ring (44). An additional mechanical finger grasp/securement device (45) can be integrated for the operator to facilitate press fitting the fusion aiding ring (44) into position. The hub/hypotube element (47) could incorporate another mated finger grasp that would be natural and easy for the operator to manage, possibly by a single hand.

Another useful feature of the non-peel-away sheath components (44, 45) may include facilitating retention of the implant to the patient's skin surface. This could be accomplished through incorporation of adhesive external retention device into a fusion ring assembly (44) or finger grasp/retention assembly (45). Another method could incorporate that the mechanical press fitting of a fusion ring (44) to the rigid hypotubes (49,102) for fusing single lumen (35b) or dual lumen catheters (42) activates deployment of a mechanical retention device that could include semi permanent tissue barbs or sutures. In another conception, the removable dilator (50) could be utilized to deploy a suture mediated retention of some portion of the fusion ring (44) or finger grasp/retention device (45) to the patient's skin.

In the end the fusion ring (44) is integrated into the external portion of the implant along with the finger grasp/ retention device (45) and hub assembly (47). An additional element, a hemostatic coupling may be integrated into the finger grasp portion (45) and or other sheath elements (44, 46) accepting fitting of the sterile enclosed catheter assembly (29). Features such as mechanical cushioning derived through flexibility or possibly telescopic entry would be useful for the the mounting point of the sterile enclosed catheter assembly (29) and its front vent (32) to the sheath (43). This mounting typically will include a quick release hemostatic valve that could free the sterile enclosed catheter assembly (29) from the sheath assembly (43) quickly and with minimal motion of the sheath within the patient. The fitting of (32) to (43) should integrate well into the mechanical feedback observation window (30). Luer lock is proposed initially but any other type of easily handled and non cumbersome fitting would work. A "slip-tip" type coaxial fitting design may be preferable at this location. The hemostatic coupling portion of the finger grasp (45) may be incorporated into the mechanical fusion ring (44) or incorporated into the peel away sheath/finger grasp (46) or may be slotted and/or otherwise peeled away independently from the sheath (46).

LITERATURE CITATIONS [#]

1. Rivera A M, Strauss K W, van Zundert A, Mortier E. The history of peripheral intravenous catheters: how little plastic tubes revolutionized medicine. Acta Anaesthesiol Belg. 2005; 56(3):27182. Review.
2. Fernstrom A, Goldblatt M. Aerobiology and its role in the transmission of infectious diseases. J Pathog. 2013; 2013: 493960. doi: 10.1155/2013/493960. Epub 2013 Jan. 13.
3. Neuman M L, Murphy B D, Rosen M P. Bedside placement of peripherally inserted central catheters: a cost effectiveness analysis. Radiology. 1998 February; 206(2): 4238.
4. Stuart R L, Cameron D R, Scott C, Kotsanas D, Grayson M L, Korman T M, Gillespie E E, Johnson P D. Peripheral intravenous catheter associated *Staphylococcus aureus* bacteraemia: more than 5 years of prospective data from two tertiary health services. Med J Aust. 2013 Jun. 3; 198(10):5513.
5. Moran J, Colbert C Y, Song J, Mathews J, Arroliga A C, Varghees S, Hull J, Reddy S. Screening for novel risk factors related to peripherally inserted central catheter associated complications. J Hosp Med. 2014 August; 9(8):4819. doi: 10.1002/jhm.2207. Epub 2014 Jun. 9.
6. CDC Newsroom Press Release: CDC and Partners Celebrate World Health Day 2011 to Draw Attention to the Issue. Apr. 7, 2011 http://www.cdc.gov/media/releases/2011/p0407_antimicrobialresistance.html
7. CDC Guidelines for the Prevention of Intravascular Catheter Related Infections, 2011.
8. A Multifactorial Intervention for Reducing Catheter Related Bacteremias in Intensive Care Medicine Departments. Pilot Study Report. Madrid: Ministry of Health and Consumer Affairs, 2009.
9. The Joint Commission. Preventing Central Line-Associated Bloodstream Infections: A Global Challenge, a Global Perspective. Oak Brook, I L: Joint Commission Resources, May 2012. http:www.PreventingCLABSIs.pdf.
10. Seldinger, Sven Ivar (1953) 'Catheter Replacement of the Needle in Percutaneous Arteriography: A new technique', Acta Radiologica [Old Series], 39:5, 368-376

What is claimed:

1. A method of placing a catheter inside a body, comprising: providing an enclosed tube comprising a guidewire and one or more external magnets that are external to the enclosed tube and coupled to one or more ferromagnetic components within the enclosed tube; the enclosed tube open at one end to provide an entry to the body;
   wherein the one or more external magnets comprise a first external magnet that is coupled to a first ferromagnetic actuator that moves the guidewire and a second external magnet that is coupled to a second ferromagnetic actuator that moves the catheter; and
   moving at least one of the external magnets to provide a motive force to move at least a portion of the guidewire from inside the tube to inside the body; and moving a catheter over the guidewire into place within the body; and wherein, during the entire procedure, the one or more ferromagnetic components remain outside the body.

2. The method of claim 1 wherein at least one other external magnet is coupled to one or more ferromagnetic component within the tube that is, in turn, coupled to the catheter that is also within the tube; and the at least one other external magnet is moved to provide a motive force to move at least a portion of the catheter from inside the tube to inside the body.

3. The method of claim 2 wherein the guidewire is withdrawn from the body after the catheter is in place.

4. The method of claim 1 wherein the one or more external magnets provide a magnetic field that translates down the length of the enclosed tube in a proximal direction toward the body, and is are rotatable around a circumference of the tube to provide rotation about a central axis of the guidewire and/or catheter within the tube.

5. The method of claim 4 wherein the enclosed tube has an inner diameter that is 50% greater or less than an outside diameter of the catheter.

6. The method of claim 5 wherein a sterile saline solution is added through a distal end of the tube.

7. The method of claim 4 wherein, at the end of the procedure, a portion of the catheter is cut and a hub is attached to a distal end of the catheter; wherein the hub has a larger diameter than the catheter.

8. The method of claim 7 wherein an exposed end of the catheter has a fitting for attachment to an injection port.

9. The method of claim 8 wherein the catheter has several fittings along its length so that, after placement, the catheter can be cut to a desired length and still be attached to an injection port.

10. The method of claim 1 where an operator manipulates the catheter and guidewire independently using one hand through the use of an integrated handgrip.

11. A catheter placement apparatus, comprising:
    a sterile enclosed tube comprising: a guidewire, a first ferromagnetic component coupled to the guidewire, and a catheter, all of which are disposed within the sterile enclosed tube;
    one or more external magnets that are mounted to an exterior of the sterile enclosed tube and coupled to one or more ferromagnetic components within the sterile enclosed tube;
    and wherein a largest dimension of the enclosed tube is a length direction and wherein the one or more external magnets comprises: a first external magnet that is coupled to the first ferromagnetic component that is coupled to the guidewire and a second external magnet that is coupled to a second ferromagnetic actuator that is coupled to the catheter; and wherein the first external magnet is translatable in the length direction of the enclosed tube.

12. The catheter placement apparatus of claim 11, wherein the enclosed tube is configured to open at at least one end to provide access to a body.

13. The catheter placement apparatus of claim 12 comprising a gauge that measures a resistance encountered by the guidewire.

14. The catheter placement apparatus of claim 13 wherein the gauge comprises a transparent window disposed on a proximal end of the enclosed tube such that the guidewire can be seen through the transparent window.

15. The catheter placement apparatus of claim 12 further comprising a handgrasp disposed at the proximal side of the apparatus that includes controls for moving the guidewire and/or catheter in translation and/or rotation.

16. The catheter placement apparatus of claim 11 comprising a generally planar tube support and mount assembly that holds the enclosed tube to the tube support.

17. The catheter placement apparatus of claim 16 comprising a power source and one or more motion control computers to aid in moving the one or more external magnets.

18. The catheter placement apparatus of claim 11 wherein the first external magnet or the second external magnet comprises a Halbach array of magnets.

19. The catheter placement apparatus of claim 11 wherein the first external magnet or the second external magnet has a magnetic field that is rotatable in a direction around a circumference of the enclosed tube.

20. The catheter placement apparatus of claim 11 wherein the first external magnet and the second external magnet are translatable in a length direction of the enclosed tube.

21. The catheter placement apparatus of claim 11 wherein the first ferromagnetic actuator is integral with the guidewire and wherein the second ferromagnetic actuator is integral with the catheter.

22. A catheter placement apparatus, comprising:
a sterile enclosed tube comprising: a guidewire, a first ferromagnetic component coupled to the guidewire, and a catheter, all of which are disposed within the sterile enclosed tube;
one or more external magnets that are external to the enclosed tube and coupled to one or more ferromagnetic components within the sterile tube;
and wherein a largest dimension of the enclosed tube is a length direction and wherein the one or more external magnets comprises: a first external magnet that is coupled to the first ferromagnetic component that is coupled to the guidewire and wherein the first external magnet is translatable in the length direction of the enclosed tube and a second external magnet that is coupled to a second ferromagnetic actuator that is coupled to the catheter; and further comprising a handgrasp disposed at a proximal side of the apparatus that includes controls for moving the guidewire and/or catheter in translation and/or rotation.

* * * * *